(12) United States Patent
Bern et al.

(10) Patent No.: US 7,708,687 B2
(45) Date of Patent: May 4, 2010

(54) ENDOSCOPE PROPULSION SYSTEM AND METHOD

(76) Inventors: M. Jonathan Bern, 4931 Fawn Dell Rd., Roanoke, VA (US) 24014; James C. Peacock, III, 3317 Melendy Dr., San Carlos, CA (US) 94070

( * ) Notice: Subject to any disclaimer, the term of this patent is extended or adjusted under 35 U.S.C. 154(b) by 836 days.

(21) Appl. No.: 11/140,595

(22) Filed: May 27, 2005

(65) Prior Publication Data
US 2006/0270901 A1 Nov. 30, 2006

(51) Int. Cl.
*A61B 1/00* (2006.01)
(52) U.S. Cl. ........................ 600/115; 600/114
(58) Field of Classification Search ................ 600/101, 600/104, 114, 115, 121, 207, 208; 128/898; 180/9.1
See application file for complete search history.

(56) References Cited

U.S. PATENT DOCUMENTS

| | | | |
|---|---|---|---|
| 4,050,600 A | | 9/1977 | Jennings |
| 4,117,847 A | | 10/1978 | Clayton |
| 4,207,872 A | | 6/1980 | Meiri et al. |
| 4,368,739 A | | 1/1983 | Nelson, Jr. |
| 4,776,845 A | | 10/1988 | Davis |
| 5,331,975 A | | 7/1994 | Bonutti |
| 6,077,219 A | * | 6/2000 | Viebach et al. .............. 600/114 |
| 6,086,603 A | | 7/2000 | Termin et al. |
| 6,971,990 B2 | * | 12/2005 | Ziegler et al. .............. 600/114 |
| 7,041,051 B2 | * | 5/2006 | Bernstein .................... 600/114 |
| 7,044,245 B2 | * | 5/2006 | Anhalt et al. ................ 180/9.1 |
| 7,056,283 B2 | * | 6/2006 | Bar or et al. ................ 600/114 |
| 7,172,552 B2 | * | 2/2007 | Wendlandt .................. 600/114 |
| 2001/0008952 A1 | * | 7/2001 | Takada ....................... 600/114 |
| 2002/0143237 A1 | | 10/2002 | Oneda et al. |
| 2003/0105386 A1 | | 6/2003 | Voloshin et al. |
| 2003/0214579 A1 | | 11/2003 | Iddan |
| 2003/0225433 A1 | | 12/2003 | Nakao |
| 2004/0106976 A1 | | 6/2004 | Bailey et al. |
| 2004/0138689 A1 | | 7/2004 | Bonutti |
| 2004/0204702 A1 | | 10/2004 | Ziegler et al. |
| 2006/0020164 A1 | * | 1/2006 | Butler et al. ................ 600/115 |
| 2006/0264707 A1 | * | 11/2006 | Kinney ....................... 600/115 |

* cited by examiner

*Primary Examiner*—John P Leubecker
*Assistant Examiner*—Victoria W Chen
(74) *Attorney, Agent, or Firm*—Latimer & Mayberry IP Law, LLP

(57) ABSTRACT

A system and method provides active propulsion of endoscopes along body lumens. The propulsion system can be attached to a commercially available endoscope, or be provide affixed together, and moves the endoscope in a lumen by pulling it forward. A rotatable toroidal wall, e.g. annular invaginated balloon, provides the propulsion. A drive assembly rotates the toroid while maintaining the toroid's position along the endoscope. The toroid is radially extended or inflated within the lumen to engage its outer surface to the lumen. The toroidal rotation tracks the lumen wall for propulsion. Stops maintain the rotating toroid's position on the endoscope. A helical screw within the toroid engages patterned protrusions around the toroid; screw rotation advances the protrusions to rotate the toroid wall. A fitted belt coupled to a groove in the toroid provides alternative actuation. Colonoscopy is substantially improved, reducing anesthesia and other requirements and costs, and improving safety.

21 Claims, 17 Drawing Sheets

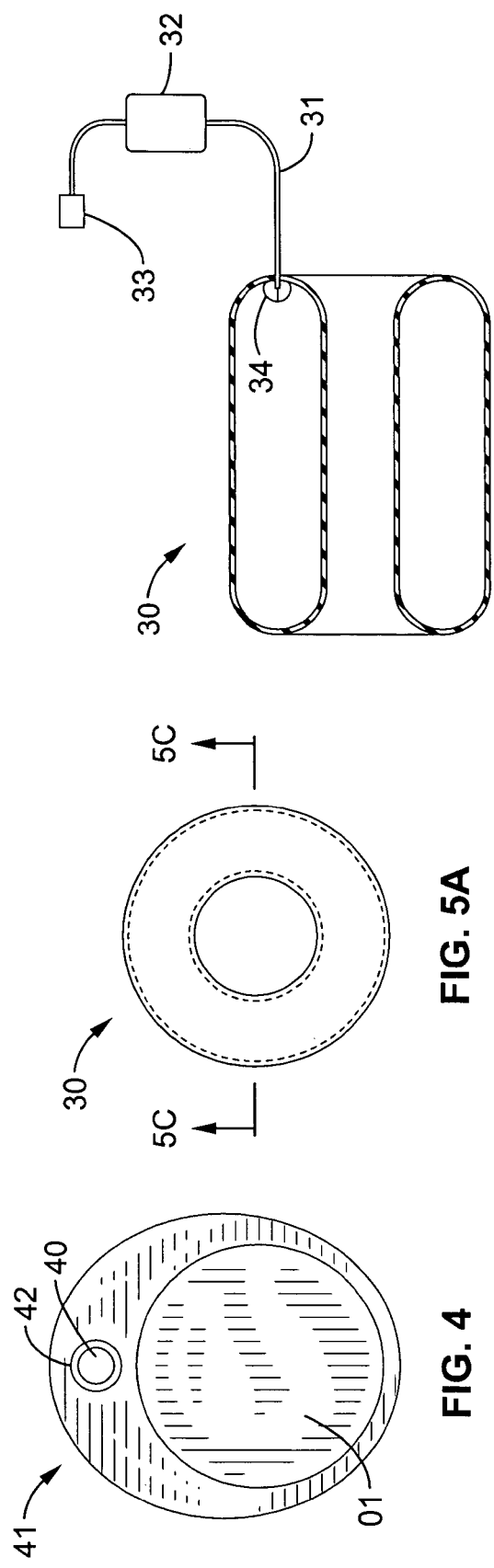

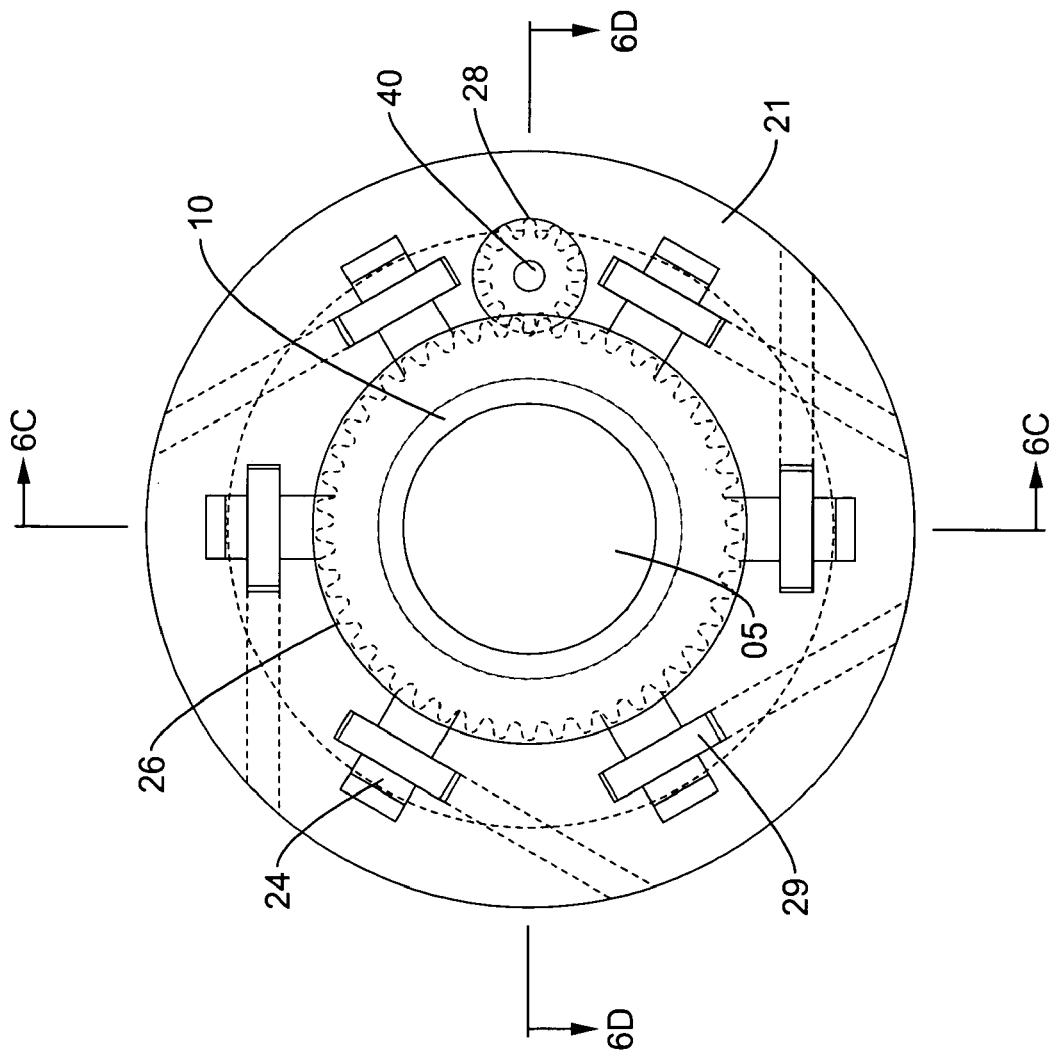

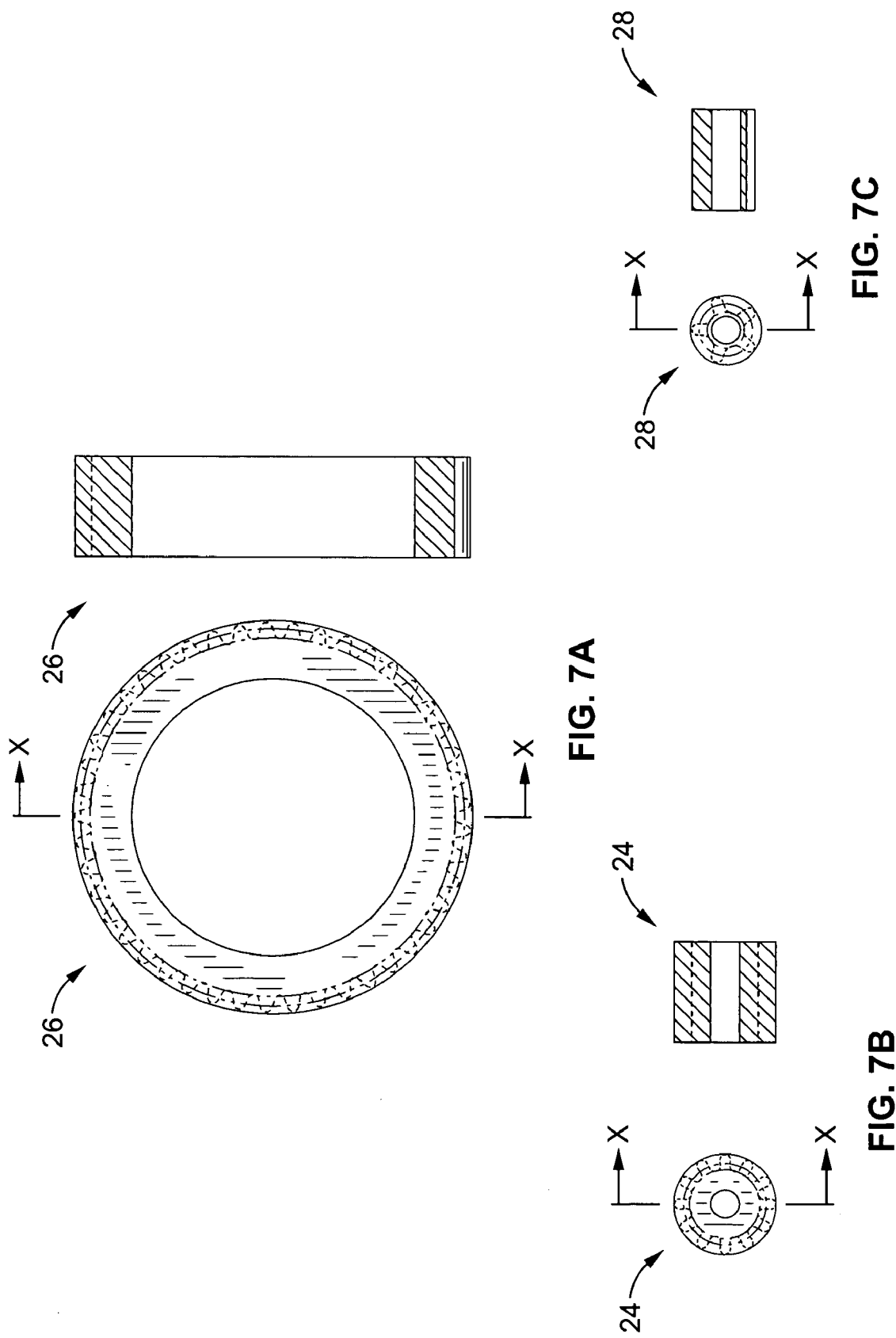

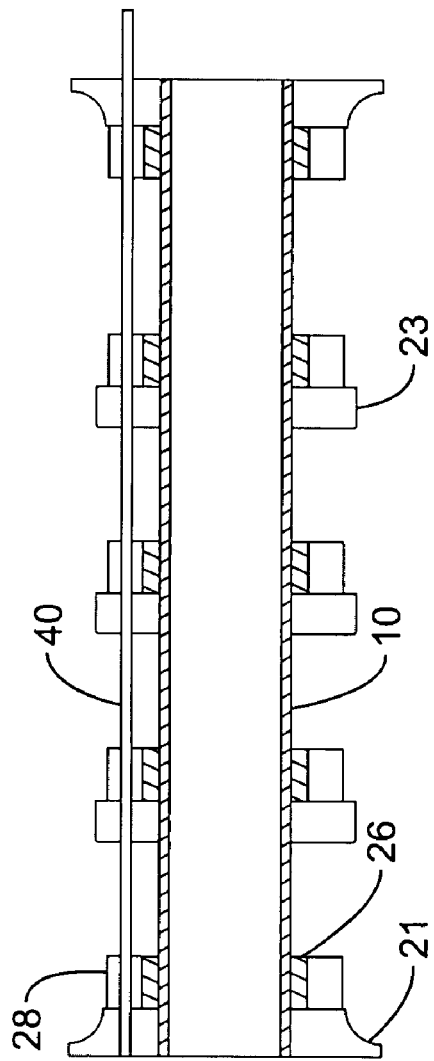
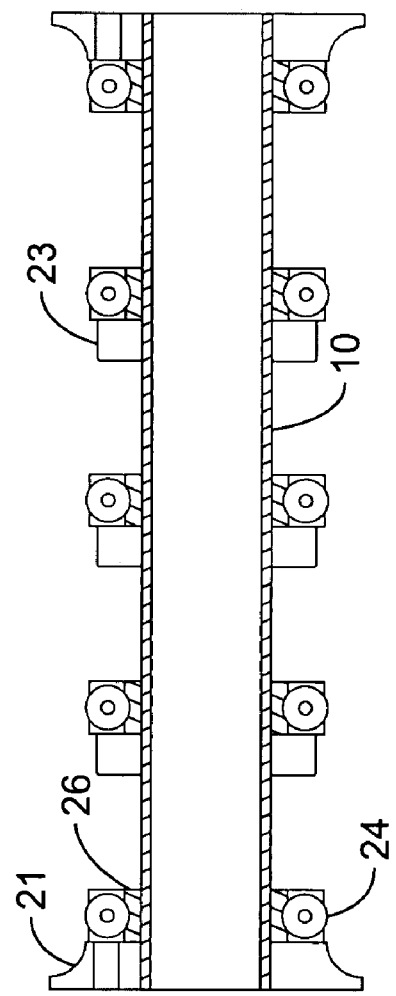

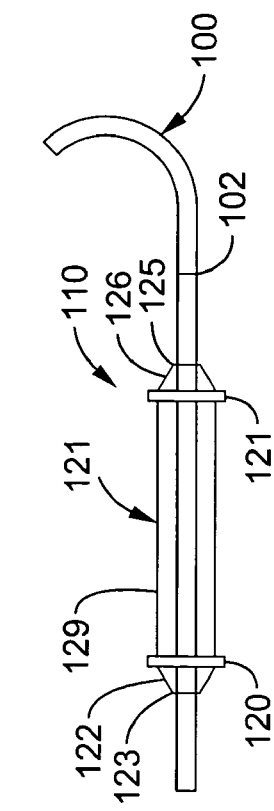
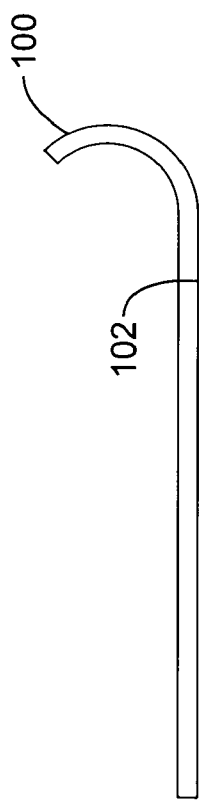
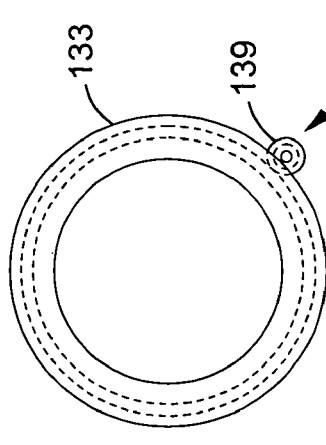
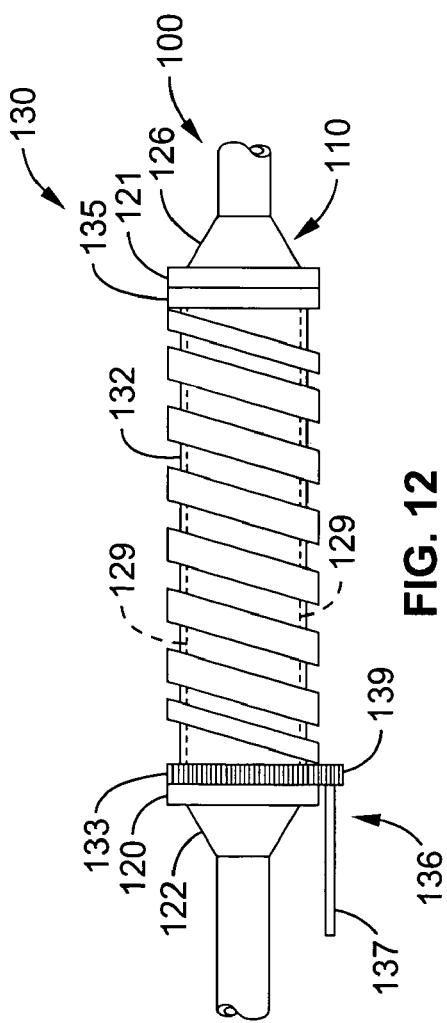

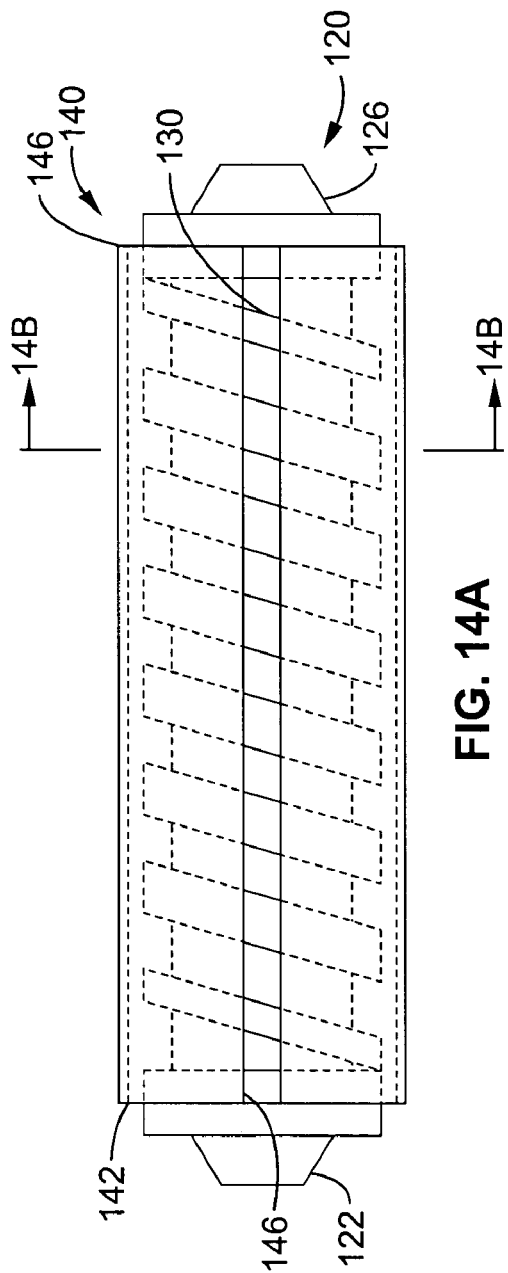
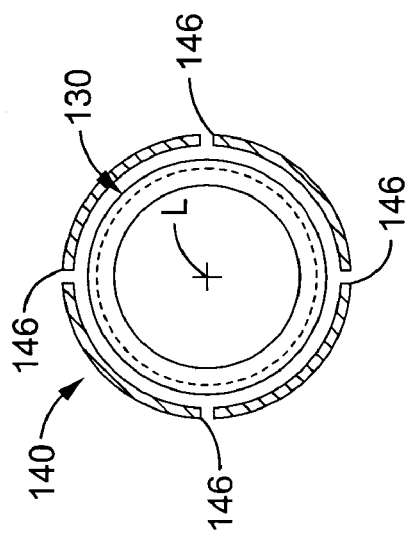
FIG. 14A
FIG. 14B

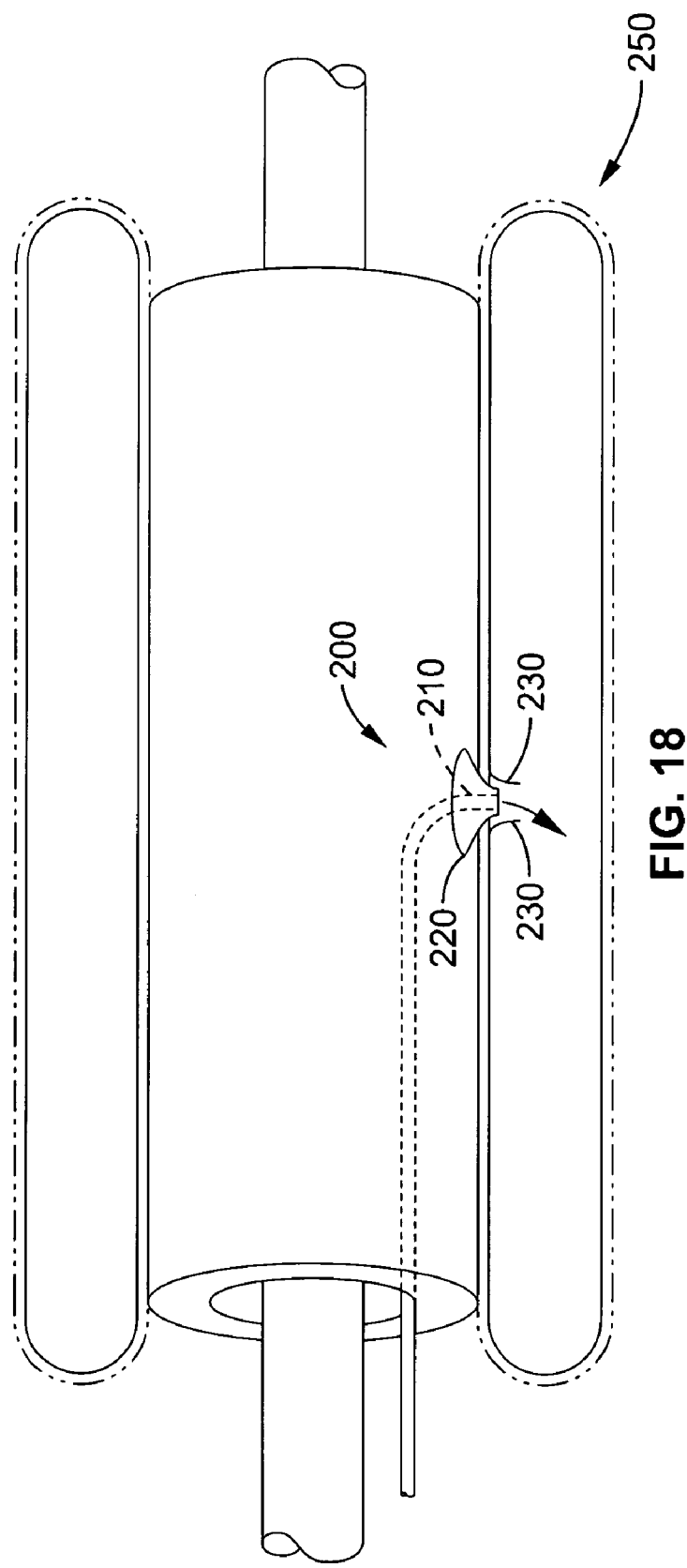

ENDOSCOPE PROPULSION SYSTEM AND METHOD

CROSS-REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

This present invention provides a system and method adapted to assist movement of devices through body spaces, and in particular body lumens. More specifically, it provides a system and method adapted to assist endoscope movement along body spaces such as lumens. Still more specifically, it provides a system and method adapted to assist movement of devices, and in particular endoscopes, through the colon and lower gastrointestinal tract.

2. Description of Related Art

Each year 60,000 Americans die from colon cancer, making colon cancer the second leading cause of cancer death in the United States. Early detection of the disease greatly improves survival. Furthermore, removal of pre-cancerous polyps can be achieved endoscopically which prevents colon cancer altogether. Unfortunately early colon cancer and polyps are asymptotic. For this reason screening tests are needed to detect and prevent colon cancer. Currently available screening tests include fecal occult blood test, flexible sigmoidoscopy and colonoscopy. In part because of the limitations of these tests only about 10% of the United States population is currently screened for this common preventable cause of death.

Fecal occult blood testing detects blood in the stool that can not be seen on visual inspection of the stool. Unfortunately only about 30% of colon cancers can be detected by fecal occult blood testing, making this test too insensitive for effective screening.

Flexible sigmoidoscopy is a type of endoscopy that uses a semi-rigid tube with fiberoptic lenses to directly visualize the colon. The end of this semi-rigid tube has a flexible steering section to direct the instrument's tip. In an ideal patient this test can visualize up to 60 centimeters of the distal colon (or approximately one-third of the entire colon). The limited extent of the flexible sigmoidoscopy exam misses approximately 50% of colon cancers. Although flexible sigmoidoscopy is insensitive it is relatively inexpensive and can be performed as a screening test in a physician's office. Unfortunately flexible sigmoidoscopy is too uncomfortable for many patients to tolerate. Flexible sigmoidoscopy is painful because the scope is advanced in the colon by pushing the semi-rigid tube against the colon wall. As the tube is pushed against the colon wall, the colon is stretched. Stretching of the colon causes intense visceral pain. In addition to pain stretching the colon too far can result in colon perforation, a potentially life threatening complication of flexible sigmoidoscopy.

Colonoscopy like flexible sigmoidoscopy is a type of endoscopy that utilizes a semi-rigid tube with either fiberoptic lenses or a video camera to directly visualize the colon. Currently available colonoscopes offer an excellent view of the colon. In a fashion similar to flexible sigmoidoscopy the semi-rigid tube has a flexible steering section at the distal end of the instrument. Unlike the flexible sigmoidoscope, the colonoscope is long enough to visualize the entire colon. For this reason colonoscopy is ideal for colon cancer screening. If a pre-cancerous colon polyp is detected at the time of colonoscopy it can be removed through the scope's "working channel" using various endosurgical instruments (such as biopsy forceps and polypectomy snares). In a fashion similar to flexible sigmoidoscopy, pushing the semi-rigid tube against the colon wall advances the colonoscope. Unfortunately colonoscopy is far too uncomfortable to be performed without high level intravenous sedation or general anesthesia. The pain experienced during colonoscopy is related to stretching of the colon wall as the colonoscope is advanced. Colon perforation can occur as a result of pushing the semi-rigid tube too forcefully against the colon wall as the colonoscope is advanced. The high level of sedation needed for colonoscopy requires a highly monitored environment such as an operating room. With the added operating room charges colonoscopy becomes quite costly. If colonoscopy were less expensive it would be more widely accepted as a colon cancer-screening test.

The purpose of the current invention is to develop a safe and effective low cost method for colon cancer screening. To achieve this end the inventors have developed an endoscopic propulsion unit that can attach to currently available colonoscopes. The endoscopic propulsion unit will advance a colonoscope in the colon lumen without stretching the colon wall; greatly reducing procedure-related pain. In addition, safety of colonoscopy will be improved by eliminating the risk of colon perforation. The endoscopic propulsion unit advances a colonoscope by pulling the distal end of the instrument. The invention that follows will allow relatively painless colonoscopy that can be performed safely in a physician's office. By removing the need for high level sedation, colonoscopy could be moved to a lower cost center such as a physician's office. This could result in a 66% savings in the total colonoscopy cost. It is hoped that this comfortable, effective, affordable and safe method for colon cancer screening will be widely used to reduce colon cancer mortality.

Various robotic endoscopy devices and methods have been previously disclosed. Several such disclosures involve robotic endoscopes that are generally complex devices with multiple interacting segments. These previously disclosed robotic endoscopes generally involve a kinematically redundant robot, which generally has about seven or more internal degrees of freedom. These robotic endoscopes are also designed to function autonomously as a robot. An examining physician has no direct control of the robotic endoscope. Furthermore the examining physician cannot directly assist in the movement of the scope in an organ lumen. The lack of direct physician control will markedly increase the risks of robotic endoscopy.

The previously disclosed robotic endoscopes also depend on a complicated interaction of a plurality of segments. At least one previously disclosure involves a robotic endoscope that relies on a complex array of pressure sensors, gripping devices and expansion modules under the control of at least one computer. Even the slightest malfunction of the complex control mechanism could cause devastating complications for a patient.

More specifically, the prior robotic endoscope uses a proximal and a distal toroidal balloon in conjunction with an extensor module. The proximal toroidal balloon expands to statically grip the organ wall and thereby fix this segment of the robotic endoscope to the organ wall. After the proximal balloon has expanded, the extensor module expands thus lengthening the robotic endoscope. The robotic depends primarily on the extensor module for movement. After the extensor module has lengthened the robotic endoscope, the distal toroidal balloon expands to fix this segment of the robotic endoscope to the organ lumen wall. After distal toroidal balloon inflation, the proximal toroidal balloon deflates and the extensor module contracts. This arrangement is said to produce an inch-worm-like movement in an organ lumen.

The toroidal balloon described in at least two such prior disclosures operates by means of static friction. This static friction is fundamental to the operation of the robotic endoscope. This static friction is between the balloon and organ wall. The only dynamic feature of the toroidal balloon's operation is expansion and contraction. Extension and contraction of the extensor module causes movement of the robotic endoscope in an organ lumen. As such, the extensor module is the main dynamic component of the robotic endoscope.

The toroidal balloon(s) described in at least these two prior disclosures involves a relatively small surface area. Thus high inflation pressures may be required to grip and fix the toroidal balloon to the organ wall. A high inflation pressure used to fix the toroidal balloon to an organ wall may distend the organ wall. This degree of organ wall distention may produce intense visceral pain. Therefore, robotic endoscopy according to these prior devices and methods may often require high level sedation or general anesthesia to permit a comfortable examination. In this regard, robotic endoscopy according to these prior disclosures offers no additional benefits to currently available endoscopic procedures.

Furthermore, the extensor module of these prior robotic endoscope disclosures is constantly changing the axial length of the robotic endoscope. As the robotic endoscope is constantly changing length, currently available endosurgical devices such as biopsy forceps or polypectomy snares may be very difficult if not prevented from conjunctive use.

The mechanical complexity of this prior approach and the need for computer control systems generally relate to relatively high production cost for the robotic endoscope. And, as in many fields, high production cost could substantially limit the availability of robotic endoscopy for widespread clinical use, such as in colorectal cancer screening. Moreover, sufficiently high production cost may also prohibit disposal of the robotic endoscope after each use. As disposal would not be generally practical according to these prior approaches, sterilization of the robotic endoscope becomes a likely necessity. Furthermore, sterilizing such a complex device with multiple mechanical and electronic components would be still a further challenge of substantial difficulty. The difficulty in sterilizing these robotic endoscopes may result in elevated potential for infectious disease transmission.

Other medical devices have also been previously disclosed that operate, at least in part, in much the same fashion as the robotic endoscopes just described. At least one additional medical device has been disclosed that uses an expandable front and rear cuff section with an expandable center section to produce movement, sharing certain similarities, including various of the incumbent shortcomings and concerns, with the robotic endoscope noted above. Another lumen-traversing device has also been disclosed that also shares certain similar limitations as the robotic endoscopes noted.

The disclosures of the following issued U.S. Patents are herein incorporated in their entirety by reference thereto: U.S. Pat. No. 4,117,847 to Clayton; U.S. Pat. No. 4,207,872 to Meiri et al.; U.S. Pat. No. 4,321,915 to Leighton et al.; U.S. Pat. No. 4,368,739 to Nelson, Jr.; U.S. Pat. No. 4,561,427 to Takada; U.S. Pat. No. 4,615,331 to Kramann; U.S. Pat. No. 4,676,228 to Krasner et al.; U.S. Pat. No. 4,776,845 to Davis; U.S. Pat. No. 5,236,423 to Mix et al.; U.S. Pat. No. 5,259,364 to Bob et al.; U.S. Pat. No. 5,331,975 to Bonutti; U.S. Pat. No. 5,337,732 to Grundfest et al.; U.S. Pat. No. 5,398,670 to Ortiz et al.; U.S. Pat. No. 5,562,601 to Takada; U.S. Pat. No. 5,586,968 to Grundl et al.; U.S. Pat. No. 5,662,587 to Grundfest et al.; U.S. Pat. No. 6,071,234 to Takada; U.S. Pat. No. 6,086,603 to Termin et al.; and U.S. Pat. No. 6,224,544 to Takada.

The following U.S. Patent Application Publications are also herein incorporated in their entirety by reference thereto: US 2002/0143237 to Oneda et al.; US 2003/0225433 to Nakao; US 2004/0106976 to Bailey et al.; and US 2004/0138689 to Bonutti.

There is still a need for improved endoscope delivery, in particular relation to colonoscopy.

There is in particular still a need for improved system and method that actively propels endoscopes within tortuous body lumens, and in particular the colon and lower GI tract, with improved control and substantially reduced wall trauma and pain.

There is also still a need for an improved system and method that modifies commercially available endoscopes for active propulsion along body lumens.

BRIEF SUMMARY OF THE INVENTION

One aspect of the present invention is a device and related method that is adapted to assist movement of a commercially available endoscope in an organ lumen.

According to one mode, the device uses an external variable speed motor to provide torque. In one embodiment of this mode, an external control unit regulates rotational direction and speed. In a further embodiment, torque from the motor is transmitted to a flexible drive shaft that, according to one variation, runs through a slip coupling. In another further embodiment, the drive shaft is contained within a sheath that runs substantially along the length of the endoscope. In another further embodiment, the sheath is attached to the endoscope by brackets. In another further embodiment, the drive shaft is attached to an internal drive gear contained within a transmission.

In still a further transmission embodiment, the transmission comprises an internal drive gear, an intermediate gear, and an external drive gear, which are adapted to cooperate together, e.g. with various supports and couplings, necessary to allow for interaction and rotation of the individual gears. The internal drive gear turns an intermediate gear. According to one further feature, the intermediate gear may be held in position by bearing, which may include in one further embodiment a flexible tube. According to one variation of this feature, the flexible tube is coupled to the distal end of an endoscope, such as in one highly beneficial variation by attachment means that may include for example attachment brackets. Rotation of the intermediate drive gear causes rotation of external drive gears. The external drive gears are radially arrayed on the outside of the flexible tube. The external drive gears are in contact with the inner surface of an annular invaginating balloon. The annular invaginating balloon is donut shaped in cross-section with a length that may be adapted and varied in dimension to suit one or more particular applications. Interaction of the external drive gears with the annular invaginating balloon actuates rotation of the annular invaginating balloon along its long axis. The annular invaginating balloon is inflated after insertion into an organ lumen. This is accomplished in one particular variation by use of a cannula and a syringe. A sensor and/or indicator is provided that allows control of inflation to a desired parameter, such as for example pressure or volume. In one particular beneficial embodiment, a pressure sensor, which according to one variation may include a pressure-sensing bulb on the cannula, is adapted to allow control to an appropriate inflation pressure. After the annular invaginating balloon has been inflated to the appropriate pressure and/or other parameter such as volume, the cannula and pressure-sensing bulb (if provided) is removed. A valve, such as a self-sealing valve on the annular invaginating balloon, maintains pressure within the balloon. The annular invaginating balloon is in contact with the lumenal side of an organ wall. Interaction between the annular invaginating balloon and the lumenal wall produces dynamic rolling traction (like a tire or wheel). This rolling traction in turn moves the endoscope within the organ lumen.

Another aspect of the invention provides a delivery assembly that works in conjunction with endoscopes, such as for example currently available endoscopes.

Another aspect of the current invention provides a delivery assembly that attaches easily to currently available endoscopes without generally requiring modification of such endoscopes.

Another aspect of the current invention provides an endoscope delivery assembly that is easily used and requires minimal training of the endoscopist.

Another aspect of the current invention provides an endoscope delivery assembly with an annular invaginating balloon that is adapted to produce rolling traction along a luminal wall to move an endoscope in the lumen.

According to one mode of this aspect, the invaginating balloon is adapted to be inflated with fluid to sufficiently low pressure such that trauma to the organ wall is substantially limited.

According to another mode, the annular invaginating balloon has a sufficiently large surface area adapted to contact the luminal wall, thereby substantially limiting the required inflation pressure to provide traction along the wall and limiting the propensity for pressure-related trauma from the assembly.

According to another mode, the annular invaginating balloon is provided as a modification to the endoscope, such as to currently available devices.

Another aspect of the invention provides an endoscope delivery assembly that is adapted to move an endoscope along a lumen by pulling the distal end of the endoscope.

According to one mode of this aspect, by pulling the distal end of the endoscope, the endoscopic delivery assembly substantially limits the stretching of the lumenal wall during delivery.

According to another aspect, an endoscope delivery assembly and method is adapted to deliver an endoscope along a luminal wall with substantially limited risk of organ wall perforation.

According to another aspect, an endoscope delivery assembly and method is provided that is adapted to substantially decrease procedure related pain. According to one mode of this aspect, the substantially decreased procedure-related pain is achieved by substantially reducing the extent to which the lumen wall is stretched during endoscope delivery.

Another aspect of the invention provides a colonoscopy system and method that incorporates a colonoscope delivery assembly.

According to one mode of this aspect, the colonoscope delivery assembly is adapted to allow enhanced patient comfort during colonoscopy with substantially limited sedation.

Another aspect of the invention provides a colonoscopy system and method that is adapted to allow colonoscopy to be performed without substantial sedation. According to one mode of this aspect, such system and method is adapted to be used at lower cost facilities, such as for example a physician's office, than is generally accepted according to other conventional colonoscopy systems and methods.

Another aspect of the invention provides an endoscope delivery assembly and method that is adapted to move an endoscope along a body lumen without substantially changing the length of the endoscope.

According to one mode of this aspect, the endoscope delivery system and method is adapted to move a commercially available endoscope in this manner.

According to another mode of this aspect, as the length of the endoscope remains substantially fixed, one or more commercially available endosurgical devices, such as in certain beneficial embodiments polypectomy snares and biopsy forceps, are provided and/or used in conjunction with the system and method.

Another aspect of the invention provides an endoscope delivery assembly that is adapted to provide for the further combination and use of endosurgical devices and methods, including for example both diagnostic and therapeutic devices and related procedures.

Another aspect of the invention provides an endoscope delivery assembly that is adapted to decrease procedure-related risk by decreasing the incidence of perforation during endoscopy. According to one mode, perforation is substantially reduced according to the assembly by pulling the endoscope at its distal end and by using an annular invaginating balloon as a tracking mechanism.

Another aspect of the invention provides an endoscope delivery assembly with an annular invaginating balloon that, in a radially collapsed configuration, has a first diameter that is sufficiently small to provide for introduction into a body lumen. After insertion, the annular invaginating balloon is inflated to a radially expanded configuration that is adapted to contact the luminal wall.

According to another aspect of the invention, an endoscope delivery assembly and method provides an invaginating balloon that has a removable inflation device. According to one mode, the removable inflation device comprises a cannula. According to another mode of this aspect, the balloon surface is sufficiently smooth so as to substantially limit risk of trauma to the lumen wall.

According to another aspect of the invention, an endoscope delivery assembly and method provides an annular invaginating balloon that circumscribes a longitudinal axis and has a cross-sectional profile substantially in the shape of a toroid. According to one highly beneficial mode of this aspect, the toroidal shape of the annular invaginating balloon has a length along the longitudinal axis that is larger than the cross-sectional diameter through a portion of the wall of the balloon in a radial axis transverse to the longitudinal axis, e.g. a length dimension that is longer than a simple toroid shaped balloon, thus forming an elongate tube with a lumen extending therethrough.

According to another aspect of the invention, an endoscope delivery assembly and method provides an annular invaginating balloon that rotates about its long axis while making contact with the respective lumen wall. In one highly beneficial mode of this aspect, the rotating annular invaginating balloon is adapted to provide for rolling traction of the assembly, and related assemblies coupled therewith, along the lumen wall.

According to another mode, the annular invaginating balloon functions like a wheel in contact with the lumen wall. The annular invaginating balloon is a dynamic part of the endoscope delivery assembly and provides rolling traction along the wall, resulting in movement of the endoscope delivery assembly and respectively coupled components and assemblies, e.g. such as an endoscope shaft or endoscope delivery cannula coupled thereto, along the lumen.

Another aspect of the invention provides an endoscope delivery assembly that is under substantial direct control of the endoscopist.

Additional aspects of the invention include various respective methods of operating the assemblies noted herein, which methods generally augment or replace various aspects of the endoscopic procedures and techniques previously available.

Another aspect of the invention provides an endoscope delivery assembly that incorporates a relatively simple machine with relatively few working parts.

Another aspect of the invention provides an endoscope delivery assembly that is sufficiently simple so as to allow for a relatively low cost of production as compared to other endoscope delivery assemblies intended to augment traversal of various tortuous lumens, such as for example the colon.

Another aspect of the invention provides an endoscope delivery assembly that is manufacturable at sufficiently low a cost production so as to allow for a disposable product.

According to one mode of this aspect, providing the endoscope delivery assembly as a disposable product substantially reduces the risk of infectious disease transmission, such as for example from one patient to another as may occur with higher cost equipment that is thus re-used over multiple patients.

Another aspect of the invention provides an endoscope delivery assembly that includes an integral sheath and at least one attachment bracket insure ease of attachment to an endoscope and safety of operation.

Another aspect of the invention is an endoscope propulsion device assembly with a toroidal wall, a drive assembly, and an endoscope coupler assembly as follows. The toroidal wall has an exterior surface and an interior surface that circumscribes an interior passageway extending along a longitudinal axis, and with a length between a proximal end and a distal end relative to the longitudinal axis. The toroidal wall is adjustable from a radially collapsed condition to a radially extended condition, respectively, transverse to the longitudinal axis. The drive assembly is adapted to couple to the toroidal wall and to impart toroidal rotation onto the toroidal wall in the radially extended condition such that the interior surface translates in a first longitudinal direction and the exterior surface translates in a second opposite longitudinal direction along the longitudinal axis. The endoscope coupler assembly is adapted to couple the toroidal wall to an endoscope extending along the interior passageway such that the toroidal wall and endoscope are adapted to be propelled together in the first direction along a body lumen during toroidal rotation of the toroidal wall when the exterior surface is engaged to a wall of the body lumen with translating force against the wall.

According to one mode of this aspect, the toroidal wall is provided in the form of a toroidal balloon. In a more detailed embodiment, this toroidal balloon has an annular invaginated balloon wall and is inflatable from the radially collapsed condition to the radially extended condition with a pressurized fluid.

In another mode, the toroidal balloon includes a protrusion extending from the balloon wall along the interior surface and into the interior passageway. The drive assembly is provided with an elongate screw extending along the longitudinal axis within the interior passageway and with a helical groove extending helically around the longitudinal axis. This helical groove is adapted to receive the protrusion within the interior passageway such that rotation of the elongate screw advances the protrusion longitudinally in the first direction along the longitudinal axis. The helical groove is thus adapted to move the interior surface in the first direction along the longitudinal axis to impart toroidal rotation to the toroidal balloon along the longitudinal axis.

According to one further embodiment of this mode, the protrusion extends from the interior surface with a relatively narrow neck and terminates interiorly within the interior passageway with an enlarged head relative to the neck.

According to another embodiment, a plurality of such protrusions are provided in a patterned group that are each spaced along a longitudinal pattern that circumscribes one lobe of the toroidal balloon along the longitudinal axis. Each protrusion of the group along the interior surface is engaged to a respective turn of the helical groove and translates longitudinally in the first direction along the rotating screw. Each said protrusion of the group along the inner surface is released therefrom the helical groove when it is translated in the first direction to a first end of the screw; whereas each said protrusion of the group along the exterior surface translates in the second opposite direction and is adapted to rotate inwardly to the inner surface and to be engaged within the helical groove of the screw at a second end thereof. Accordingly, continuous rotation of the screw continuously releases and engages respective protrusions of the patterned group at the first and second ends of the screw, respectively, to thereby continuously drive toroidal rotation of the toroidal balloon.

According to one further feature that may also be provided according to this embodiment, a plurality of such groups of protrusions is provided in respectively patterned arrays. Each of the groups of protrusions is located at a unique respective position around a circumference of the toroidal balloon transverse to the longitudinal axis.

According to another further feature, four of such groups of protrusions are provided. In still a further highly beneficial feature, these may be spaced at 90 degree intervals around the circumference transverse to the longitudinal axis.

In still another feature, a cowling with a substantially tubular body is located between the screw and the interior surface of the toroidal balloon and includes a longitudinal groove extending along the longitudinal axis between first and second ends of the screw. The protrusions are adapted to engage the helical groove of the screw through the longitudinal groove of the cowling.

In another feature related to multiple groups of protrusions, a cowling with a substantially tubular body is located between the screw and the interior surface of the toroidal balloon and with a plurality of longitudinal grooves extending along the longitudinal axis between first and second ends of the screw. The protrusions of each group are adapted to engage the helical groove of the screw through a respective one of the plurality of longitudinal grooves of the cowling.

According to another embodiment related to inflatable toroidal balloon modes of this aspect, an expansion actuator is also provided that is adapted to couple to the toroidal wall and expand the toroidal wall from the radially collapsed condition to the radially extended condition.

According to another mode, a motor is also provided that is adapted to couple to the drive assembly and to actuate the drive assembly coupled to the toroidal wall to impart toroidal rotation to the toroidal wall.

According to yet another mode, an endoscope is also provided in the system.

According to one embodiment of this mode, the endoscope and the toroidal wall are permanently secured in fixed position relative to each other via the endoscope coupler assembly.

In another embodiment, the endoscope and toroidal wall are adapted to be releasably coupled to each other via the endoscope coupler assembly.

According to another mode, the endoscope coupler assembly includes a base with a tubular member with an inner lumen extending along a length between first and second ends. The coupler assembly also includes first and second radial protrusion stops extending radially outwardly from the tubular member transverse to the longitudinal axis at each of the first and second ends, respectively. The base is adapted to be coupled to an endoscope extending along the inner lumen. The toroidal wall is adapted to be positioned at a location along the base with the tubular member located within the interior passageway and such that in the radially extended condition the toroidal wall has an inner diameter at the interior surface that is less than an outer diameter of the base at the first and second radial protrusion stops. The toroidal wall is adapted to undergo toroidal rotation at the position without substantially moving longitudinally along the base due to mechanical interference between the toroidal wall and the first and second radial protrusion stops.

According to another embodiment of the inflatable toroidal balloon mode, the drive assembly includes a belt that circumscribes one lobe of the toroidal balloon wall along the longitudinal axis and at a position around the circumference transverse to the longitudinal axis. The toroidal balloon wall includes a circumferential groove along the longitudinal axis and corresponding with the position. The belt is adapted to engage the circumferential groove along the exterior surface of the toroidal balloon wall at the position. The belt is also adapted to engage the drive assembly located within the interior passageway. The drive assembly is adapted to rotate the belt around the toroidal balloon and so as to impart translational motion to the exterior surface in the second direction to thereby provide toroidal rotation of the balloon.

In one further feature of this embodiment, the groove has a shaped interior surface with a plurality of spaced pairs of opposite protrusions into the groove to provide an alternating pattern of expanded and narrowed waste regions along the groove. The belt has a shaped outer surface with a plurality of enlargements separated by relatively narrowed waste regions. The belt and groove are adapted to couple along the exterior surface with the narrowed waste regions of the belt fitting into the narrowed waste regions of the groove. The belt is adapted to be released from the groove at first and second ends of the exterior surface along the balloon.

According to another mode, the toroidal wall comprises an elongated toroidal wall such that the length is substantially greater than a profile diameter between the interior and exterior surfaces of the toroidal wall in the radially extended condition.

Another aspect of the invention is a method for propelling an endoscope. This method includes coupling a toroidal wall to an endoscope at a location along a distal end portion of the endoscope, coupling a drive assembly to the toroidal wall at the location, and adjusting the toroidal wall from a radially collapsed condition to a radially extended condition, respectively, transverse to the longitudinal axis at the location. The drive assembly is actuated to impart toroidal rotation onto the toroidal wall in the radially extended condition at the location such that the interior surface translates in a first longitudinal direction and the exterior surface translates in a second opposite longitudinal direction along the longitudinal axis. In addition, the toroidal wall is substantially maintained at the location along the endoscope while imparting the toroidal rotation to the toroidal wall.

According to one mode of this aspect, the endoscope and respectively coupled toroidal wall and drive assembly are inserted into a body lumen of a patient. A lumen wall of the body lumen is engaged with the exterior surface of the toroidal wall in the radially extended condition. The toroidal wall and endoscope are propelled together in the first longitudinal direction along the body lumen by imparting the toroidal rotation to the toroidal wall and thereby translating the exterior surface with force in the second opposite direction against the respectively engaged body lumen wall.

Another aspect of the invention is a method for performing endoscopy within a body lumen in a patient as follows. An endoscope assembly is inserted within the body lumen. A substantial circumference of a body lumen wall of the body lumen surrounding the endoscope is engaged with a propulsion assembly coupled to the endoscope. An axial force against the body lumen wall and around the substantial circumference is provided with the propulsion assembly. Accordingly, the endoscope is propelled along the body lumen at least in part using the axial force against the body lumen wall from the propulsion assembly.

According to further aspects of the invention, the various other aspects herein described for an endoscope delivery assembly, its construction, and the various related aspects and modes of method of operation, are suitably modified and applied to non-medical uses. In certain further modes of this aspect, such assemblies and methods are incorporated into devices and methods for visual inspection and manipulation of other tubular structures.

It is also to be appreciated that each of the foregoing aspects, modes, embodiments, variations, features, or variants on such features is to be considered independently beneficial without necessarily requiring combination with the others unless expressly stated so. Notwithstanding the foregoing, it is also further appreciated that the various combinations and sub-combinations between them, as would be apparent to one of ordinary skill in the art, are further considered independently beneficial and within the intended scope hereof.

Further aspects of the invention will be brought out in the following portions of the specification and accompanying claims below, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 4 shows a schematic illustration of the location of attachment brackets and the orientation of a drive shaft adapted for use in an endoscope delivery system of the invention.

FIG. 5A shows an end view of an annular invaginating balloon adapted for use in an endoscope delivery system of the invention.

FIG. 5B shows a cut away view of an annular invaginating balloon similar to that shown in FIG. 5A, and shows an attached inflation cannula, pressure sensor, and valve.

FIG. 5C shows another cut away view of an annular invaginating balloon similar to that shown in FIGS. 5A-B, and shows inner and outer balloon surfaces.

FIG. 6A shows a schematic illustration of an end support assembly adapted for use in an endoscope delivery assembly of the invention, and shows the placement of certain component parts.

FIG. 7A shows a perspective view of an intermediate (helical) drive wheel adapted for use in an endoscope delivery assembly of the invention.

FIG. 7B shows a perspective view of an outer drive wheel adapted for use in an endoscope delivery assembly of the invention.

FIG. 7C shows a perspective view of an inner drive wheel adapted for use in an endoscope delivery assembly of the invention.

FIG. 8B shows a schematic illustration, in a longitudinal view along the axis of a drive shaft, of certain detail of additional drive assemblies including inner drive wheels according to further aspects that are adapted for use in an endoscope delivery assembly of the invention.

FIG. 8C shows a schematic illustration of additional drive assemblies placed along a length of a support tube in a plane to include outer drive wheels, which configuration is further adapted for use in an endoscope delivery assembly of the invention.

FIG. 10 shows a schematic side view of an endoscope.

FIG. 11 shows a schematic side view of the endoscope shown in FIG. 10 in a coupled arrangement with a carriage assembly according to a further embodiment of the invention.

FIG. 12 shows a side view of further detail of the carriage assembly shown schematically in FIG. 11 in coupled arrangement with a drive gear assembly.

FIG. 13 shows an end view of the carriage assembly and drive gear assembly taken along line 13-13 in FIG. 12.

FIG. 14A shows a side view of the carriage assembly and drive gear assembly shown in FIG. 12, with the additional feature of a slotted cowling.

FIG. 14B shows a schematic end view of the respectively coupled components shown in side view in FIG. 14A.

FIG. 18 shows a schematic longitudinal side view of a further embodiment, and includes various features in shadow to highlight certain functional details within an overall assembly.

DETAILED DESCRIPTION OF THE INVENTION

Figure 1:
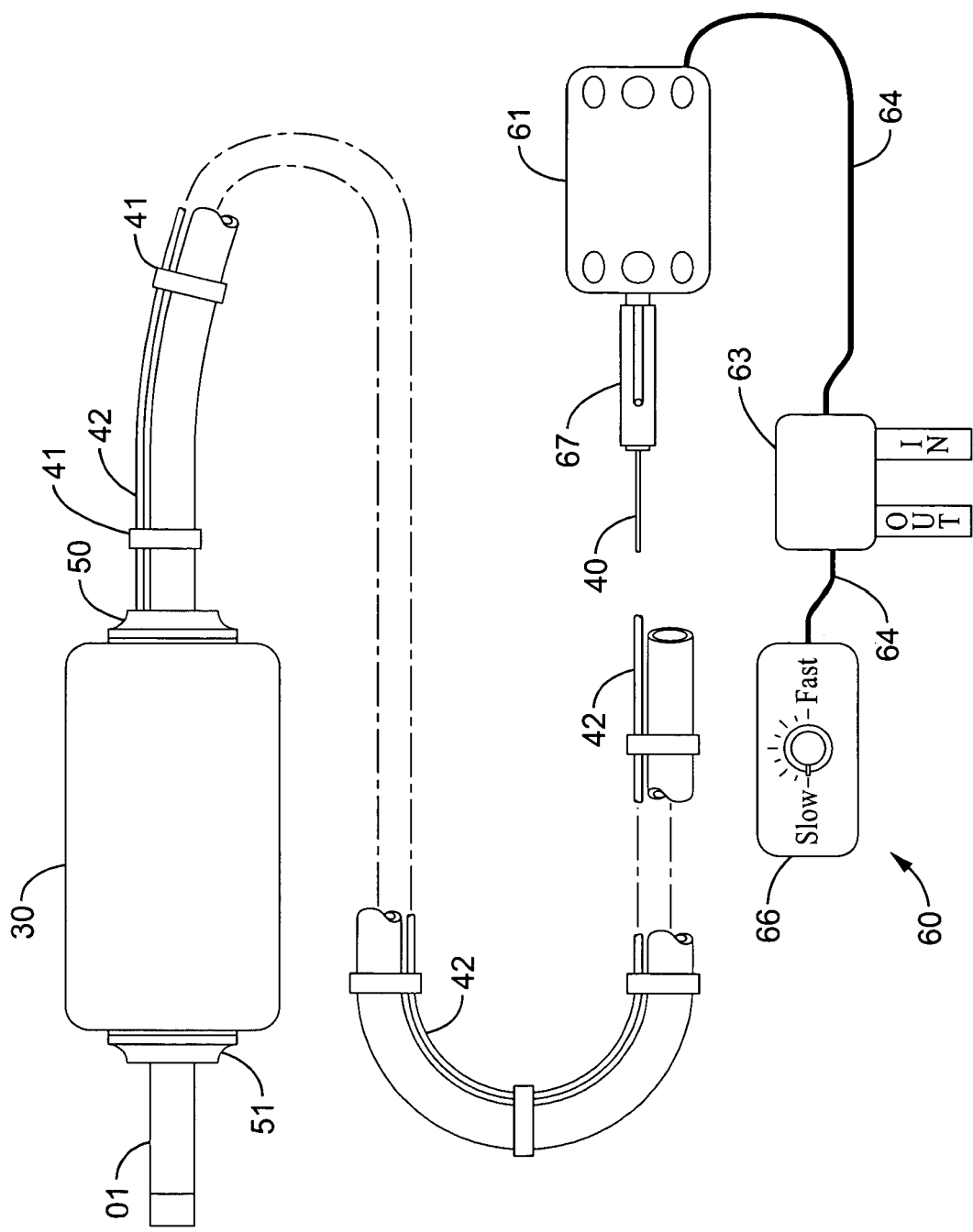
FIG. 1 shows a perspective view of a schematic illustration of an endoscope delivery system, including an endoscope delivery assembly and an external drive unit and external controls, according to one aspect of the invention.

Referring more specifically to the drawings, for illustrative purposes the present invention is embodied in the apparatus generally shown in FIG. 1 through FIG. 19. It will be appreciated that the apparatus may vary as to configuration and as to details of the parts, and that the method may vary as to the specific steps and sequence, without departing from the basic concepts as disclosed herein.

The following provide certain clarifying descriptions of the definitions intended according to certain terms and phrases, which are provided for the purpose of providing a better general understanding of the various aspects of the invention herein described.

In one regard, an "annular invaginating balloon" is generally a balloon which has a cross-sectional profile that is donut shaped like a toroid. However, in contrast to a toroid, this variation has a length that is greater than its diameter. The balloon generally functions as an active, dynamic component of an endoscope delivery assembly, and in many instances an endoscopic propulsion device, and provides rolling traction like a wheel or tire.

In another regard, an "endoscope" is generally herein intended to mean an optical or video device for examining the lumen (internal opening) of an organ.

In another regard, a "fluid" is a material that is capable of flowing, not solid of static shape and form; and may be liquid or gaseous (Funk and Wagnalle, "Standard College Dictionary" Harcourt, Brace & World cw1968).

In another regard, the term "gear" is herein intended to mean a device adapted to interact in a mechanical assembly of interacting parts that serves to transmit motion or to change the rate or direction of motion (Funk and Wagnalle, "Standard College Dictionary" Harcourt, Brace & World cw1968).

In another regard, the terms "helical gear" are herein intended to mean a gear having teeth arranged in the configuration of a helix. ("Machinery's Handbook" 25 ed., Industrial Press Inc. New York, 1996.)

In another regard, the term "motor" is herein intended to mean something that imparts or produces motion (Funk and Wagnalle, "Standard College Dictionary" Harcourt, Brace & World cw1968).

In still a further regard, the terms "pin coupling" are herein intended to mean a form of slip joint coupling to a shaft of a motor.

In yet another regard, the terms "pinion gear" are herein intended to mean a toothed wheel driving or driven by a larger cogwheel (Funk and Wagnalle, "Standard College Dictionary" Harcourt, Brace & World cw1968).

In yet still an additional regard, the terms "rolling traction" or "rotary traction" are herein intended to mean the act of drawing, as by motive power over a surface using rolling or rotational movement, respectively, such as a wheel or tire.

The term "toroid" is herein intended to mean a surface generated by the rotation of any closed plane curve about and axis lying in its plane but external to it (e.g. donut shaped) (Funk and Wagnalle, "Standard College Dictionary" Harcourt, Brace & World cw1968).

Figure 2:
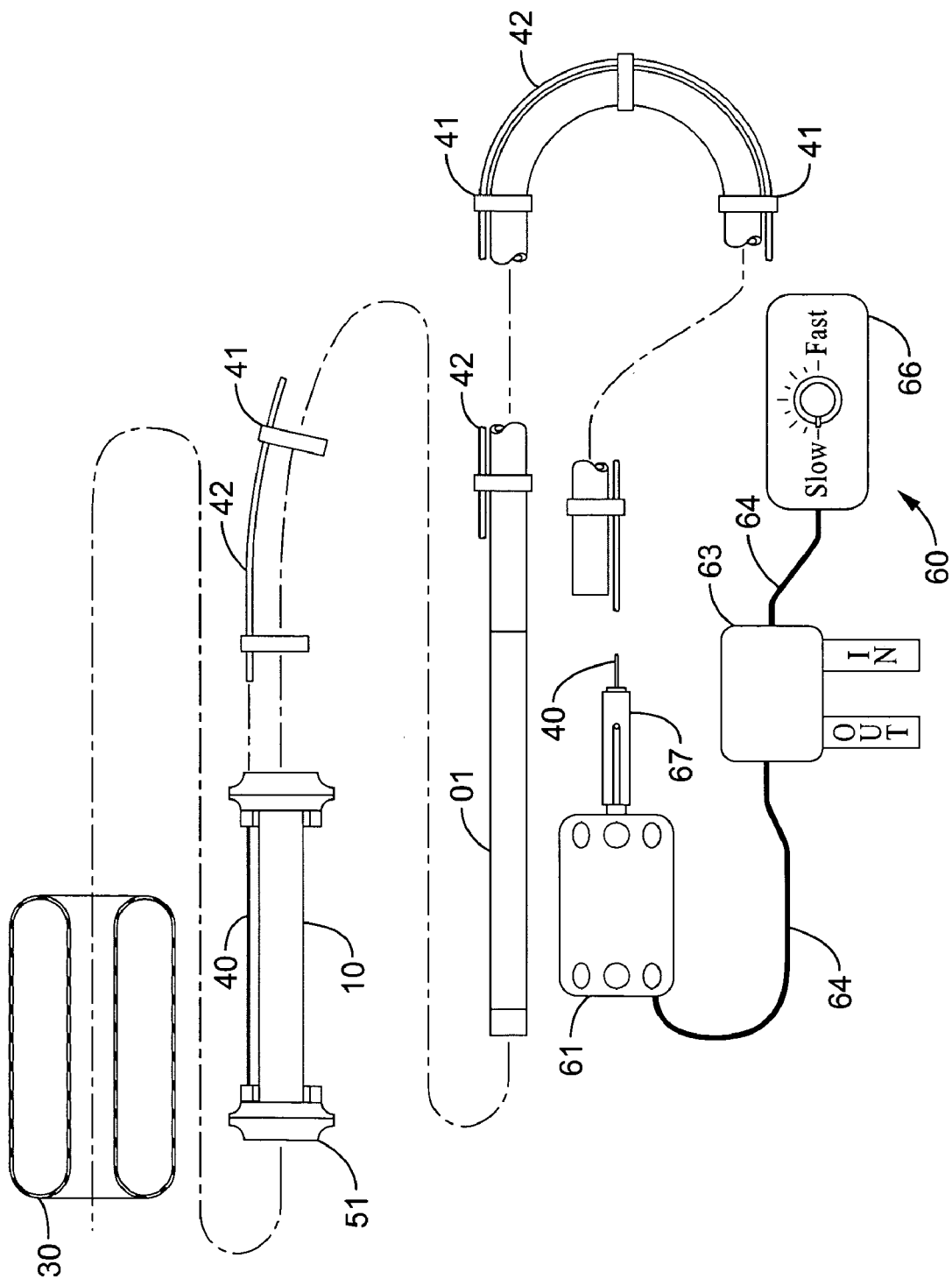
FIG. 2 shows a perspective view of a schematic illustration of an operator assembly adapted for use in an endoscope delivery system of the invention.

One highly beneficial embodiment of an endoscopic propulsion device of the present invention is illustrated in FIGS. 1 and 2. FIGS. 1 and 2 represent longitudinal views that show the component parts of the endoscopic propulsion device. FIG. 1 generally shows an entire assembled device, and FIG. 2 shows the order of assembly of the endoscopic propulsion device.

Figure 3:
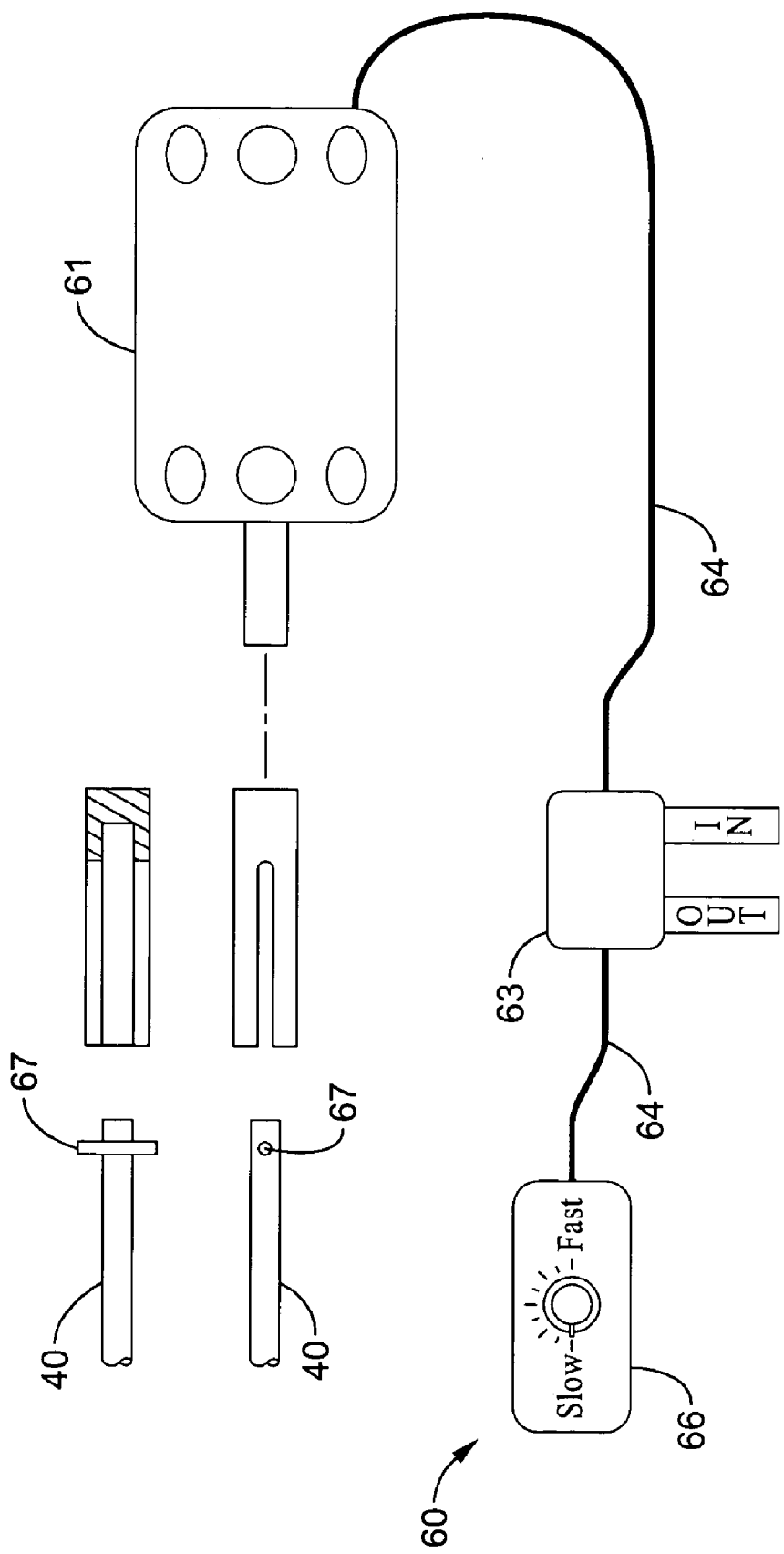
FIG. 3 shows a perspective view of a schematic illustration of an external drive unit including drive shaft coupling, external drive motor, and external controls, that is adapted for use in an endoscope delivery system according to the invention.

FIG. 3 shows external drive unit 60 that is composed of the external drive motor 61, the control unit 63, the control cables 64, the speed controller 66, and the pin coupling 67. The external drive unit 60 couples to the drive shaft 40 by means of a pin coupling 67 that acts as a torque coupler and a slip joint. While a pin coupling is utilized in the present illustrative embodiment, other means and mechanisms of drive shaft coupling may be used.

A drive shaft 40 (FIGS. 1-4) is enclosed within a drive shaft sheath 42 and is supported along the length of the endoscope by drive shaft attachment brackets 41 illustrated in FIG. 4. The drive shaft sheath prevents trauma to the organ as the drive shaft 40 turns. The drive shaft 40 enters the drive unit, transmission 25, via the proximal attachment bracket 50 and via the end support assembly 20.

Figure 6B:
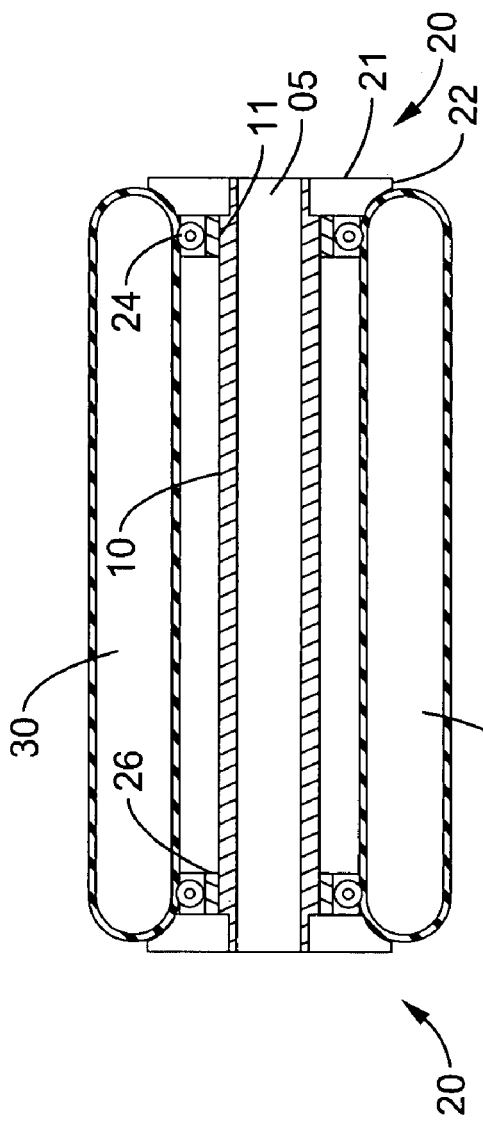
FIG. 6B shows a schematic illustration of a longitudinal mid-cross-section of an endoscope delivery assembly of the invention, and shows a longitudinal orientation of the support tube, end assemblies, a lumen for the endoscope, and an annular invaginating balloon.
Figure 6C:
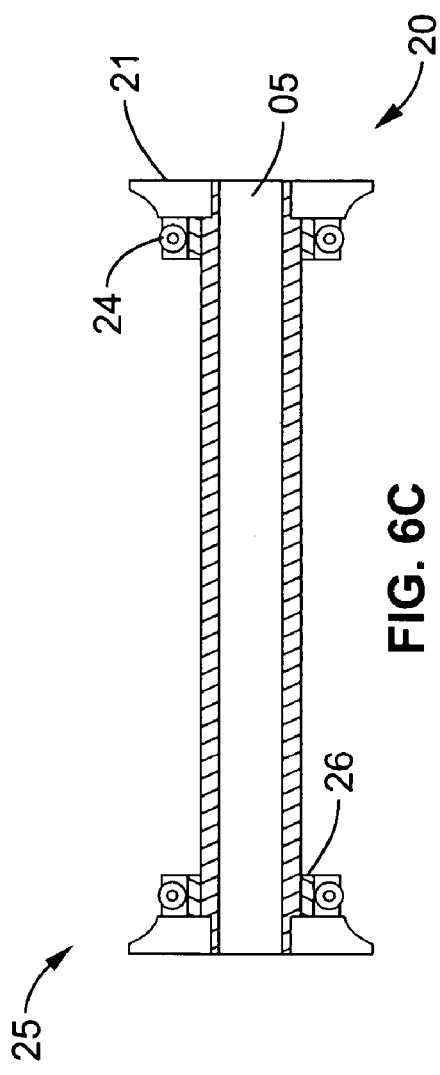
FIG. 6C shows a schematic illustration of a drive unit or transmission adapted for use with an endoscope delivery assembly of the invention, wherein the annular invaginating balloon has been omitted for clarity.

In one embodiment, the drive unit or transmission 25 shown in FIG. 6C consists of two-end support assemblies 20 each located and fixed to opposite ends of the support tube 10. The end support assemblies 20 are sub-units of the drive unit, transmission 25. In the embodiment illustrated in FIG. 6A, each end support assembly 20 is composed of the end support 21, outer drive wheels 24, an intermediate drive wheel 26, an inner drive wheel 28 and the pinion shafts 29. In the embodiment shown in FIGS. 6A-D, the drive shaft 40 is solidly attached to the inner drive wheel 28. The inner drive wheel 28 is a pinion gear in the preferred embodiment that is held in place by the end supports 21 located on both ends of the end support tube 10 and by the drive shaft 40 (FIG. 6D).

Figure 6D:
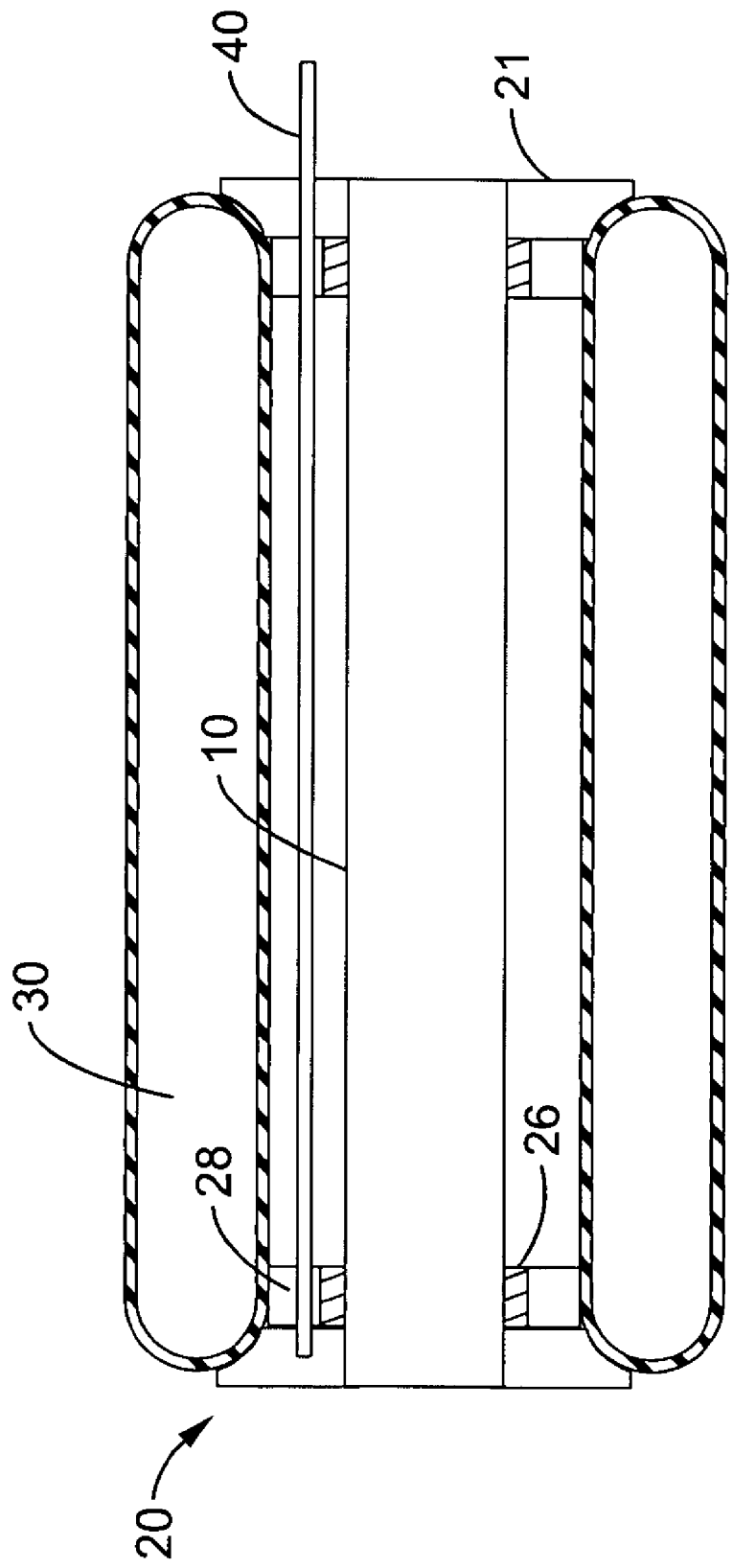
FIG. 6D shows a schematic illustration of a longitudinal mid-cross-section of an endoscope delivery assembly of the invention along the axis of a drive shaft incorporated into the delivery system.

The inner drive wheel 28 is in contact with the intermediate drive wheel 26 with sufficient friction to transmit adequate torque (FIG. 6D). The drive shaft 40 is the axle for the inner drive wheel 28. The drive shaft 40 is positioned parallel to the log axis of the support tube 10 (FIG. 6D).

In the present embodiment, the intermediate drive wheel 26 is a plastic helical gear. The intermediate drive wheel 26 is held in position on the support tube 10 by a mating groove 11 located on the external surface of the support tube 10. This groove 11 serves as the bearing for the intermediate drive wheel 26.

The outer drive wheels 24 are attached to the end support 21 in a radial array. The outer drive wheels 24 rotate in a direction parallel to the support tube 10. In the preferred embodiment, the outer drive wheels 24 are in contact with the intermediate drive wheel 26 in such a means as to allow transfer of rotational energy from the intermediate drive wheel 26 to the outer drive wheels 24 (FIG. 6B). In the present embodiment, rotational energy from the external drive wheels 24 is transmitted to the annular invaginating balloon 30 by friction.

Further to the present embodiment, such as illustrated in FIGS. 1, 5A, 6B, and 6D, an annular invaginating balloon 30 is positioned over the drive unit 25, as shown in particular in FIG. 6C. The annular invaginating balloon is held in position by the end support lips 22 located on each of the end supports 21. The inner surface of the annular invaginating balloon 35 is in contact with the outer drive wheels 24 (FIG. 6B) with sufficient friction so as to rotate the annular invaginating balloon about its long axis. The long axis of the annular invaginating balloon 30 is oriented parallel to the long axis of the endoscope 01 (FIG. 1) and the long axis of the drive unit 25 (FIG. 6C).

The annular invaginating balloon 30 is composed of contiguous inner 35 and outer 36 surfaces, as shown in FIG. 5C. The balloon 30 is constructed such that movement of the inner surface 35 translates into reactionary movement of the outer surface 36. The inner surface of the annular invaginating balloon 35 moves in response to rotation of the external drive wheels 34. This in turn moves the outer surface 36 of the annular invaginating balloon 30.

Friction between the outer surface 36 of the annular invaginating balloon 30 and the organ lumen wall results in movement of the entire drive unit 25 in the organ lumen. As the drive unit is firmly attached to the endoscope by the proximal 50 and distal 51 locking brackets, the endoscope moves in the organ lumen.

In one highly beneficial embodiment, the annular invaginating balloon 30 illustrated in FIGS. 5A-B has a detachable cannula 31 for fluid inflation, as shown in FIG. 5B. Such a balloon may be similar to a type that is currently commercially available. Manufacture of such a balloon would be adapted to include an inflation assembly. Components 31,32, 33, and 34 provide such a means for balloon inflation as one illustrative example. The cannula 31 includes a connection 33 for an inflation device such as a syringe. The cannula 31 includes an inflation bulb 32 for manual detection of filling pressure. After insertion of the endoscopic propulsion device into an organ lumen, the annular invaginating balloon 30 is inflated with fluid. Once inflated, the cannula is detached from the annular invaginating balloon 30. A self-sealing valve 34 maintains fluid pressure within the annular invaginating balloon 30 after the cannula 31 has been removed.

In the present illustrative embodiment, the endoscopic propulsion device has a flexible support tube 10 with a lumen suitable for the passage and attachment of an endoscope. FIG. 2 shows the insertion of a commercially available endoscope through the lumen of the support tube 10. In one particular embodiment, the endoscopic propulsion device attaches near the distal end of the endoscope. The drive tube 10 has support areas for the attachment of end supports 50 and 51, as shown in FIG. 2.

The endoscopic propulsion device according to various embodiments herein shown and described is adapted to enhance the capability of currently available endoscopes. The drive unit 25 and the annular invaginating balloon 30 attach near the distal end of the endoscope intended for endolumenal delivery within a body. One exemplary method and assembly is provided in further detail as follows in order to further illustrate various aspects of the present invention.

First, the operator attaches the drive shaft attachment brackets 41 with the integral sheath 42 along the length of the endoscope 01. Next, the proximal locking bracket 50 is attached to the endoscope. Next, the flexible drive shaft 40 is fed through the proximal locking bracket 50 and the sheath 42, as shown in assembled view in FIG. 2. As the drive shaft insertion nears completion, the operator will insert the endoscope through the support tube lumen 05 of the drive unit 25 to bring the drive unit 25 into its final location, as further illustrated in FIG. 2. The drive unit 25 is fixed in place on the endoscope by attachment of the distal locking bracket 51. The pin coupling 67 is attached to the end of the drive shaft and next attached to the external drive unit 60 via the pin coupling 67.

Movement, direction and speed of the endoscopic propulsion device are controlled externally by the operator using controls attached to the external drive unit 60, shown schematically in FIG. 1. Torque created by the external drive unit couples directly to the drive shaft 40 via the pin coupling 67. The direction of drive shaft rotation determines the movement direction for the endoscopic propulsion device.

Rotation of the drive shaft 40 rotates the internal drive wheel 28 that acts as a drive pinion to transmit torque to the intermediate drive wheel 26. The intermediate drive wheel is a helical gear that rotates freely about the support tube 10. Rotation of the intermediate drive wheel 26 transmits torque to the outer drive wheels 24 causing these wheels to rotate. In the highly beneficial present illustrative embodiment, the outer drive wheels 24 are pinion gears that are radially arrayed around the intermediate drive gear 26. The radial array of outer drive wheels 24 supports the inner surface of the annular invaginating balloon 35. The inner surface of the annular invaginating balloon 35 is in contact with the outer drive wheels 24 and the outer surface of the annular invaginating balloon 36. The outer surface of the annular invaginating balloon 36 is in contact with the organ lumen wall. As the outer drive wheels 24 rotate, the inner surface of the annular invaginating balloon 35 moves. Movement of the inner surface of the annular invaginating balloon 35 results in movement of the outer surface 36 of the annular invaginating balloon 30. The outer surface 36 of annular invaginating balloon 30 produces rolling traction in contact with the luminal surface of the organ wall. Movement of the inner surface 35 of the annular invaginating balloon 30 applies longitudinal forces to the end support lips 22. The end support lips 22 are firmly fixed to the endoscope 01 by their associated end supports 21 and locking brackets 50,51, respectively. As a result of this configuration, longitudinal force applied to the end support lip 22 moves the attached endoscope within the organ lumen.

The components of drive unit can be made of any material having sufficient rigidity to hold the components in proper alignment. The materials generally are chosen to have sufficient durability to handle the necessary torque. In one particular beneficial embodiment, polyvinyl chloride ("PVC") type of polymer or plastic is used. In addition or alternative to these, composite tubings or bodies may be employed, such as for example incorporating wire reinforcement fibers, winds, or braids, such as for example using stainless steel, nickel-titanium, or other wire mesh fibers laminated, embedded within, or otherwise coupled to a polymer wall or body.

In general with regard to one particular embodiment, the support tube may be made of any material having sufficient structural memory to substantially return to its native state once flexing and rotating forces are removed. In one highly beneficial further embodiment, this material is nylon plastic. The drive shaft 40 is made of a nylon wire in the preferred embodiment but other flexible material such as multi-wire flexible steel cable may be used. The annular invaginating balloon 30 is typically made of a durable flexible material, such as plastic or rubber. PVC, latex, silicone, polyurethane, or other materials similar to these may be employed. Such balloons are currently commercially available.

Figure 8A:
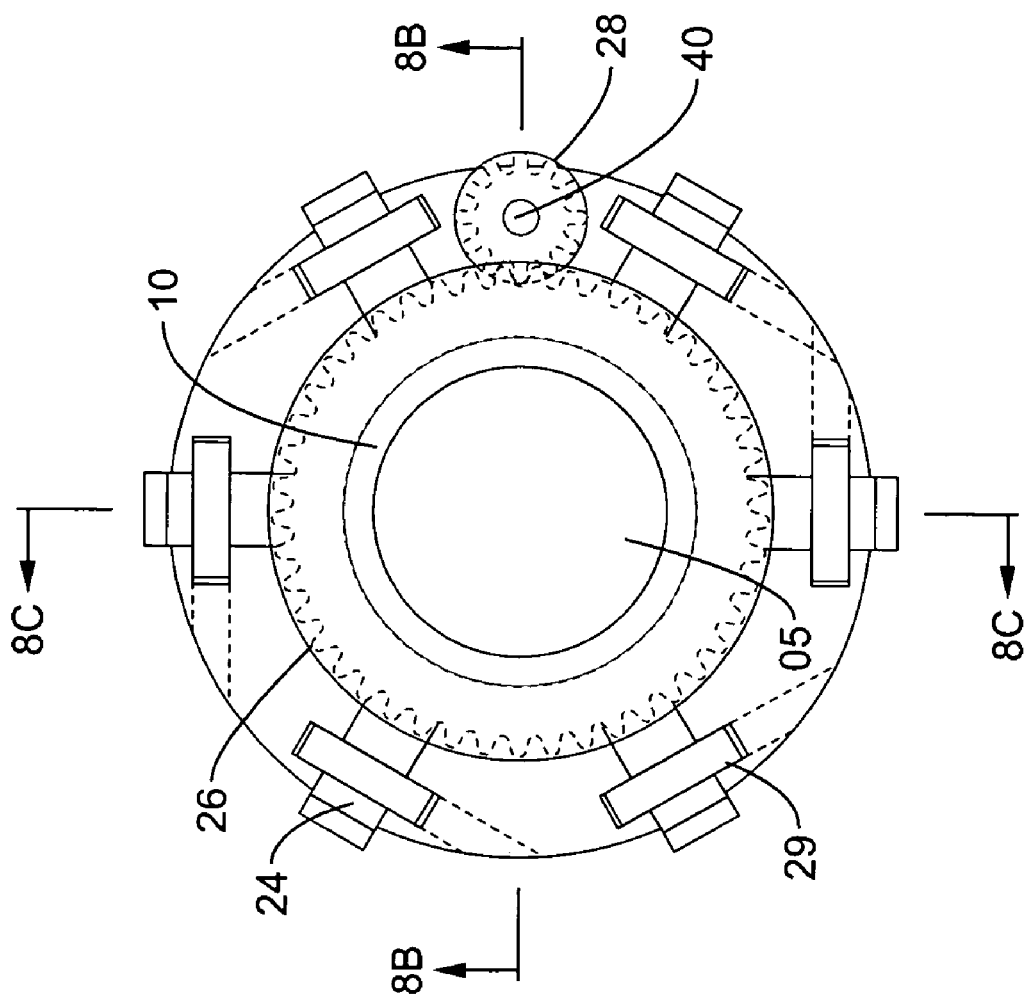
FIG. 8A shows a schematic illustration of certain cross-sectional detail of an end view of an additional drive assembly adapted for use in an endoscope delivery assembly of the invention.

An additional embodiment is shown in FIGS. 8A, 8B and 8C. This embodiment includes one or more additional intermediate drive assembly(s) placed on the tube 10 between the end support assemblies 20. The additional intermediate drive assemblies consist of the intermediate drive support 23, an inner drive wheel 28, an intermediate drive wheel 26 and outer drive wheels 24. An intermediate drive assembly is similar in construction and function to the end drive assembly 20. The intermediate drive support 23 consists of a durable material such as plastic, which may for example be of similar construction to the end support assembly 20. The intermediate drive assembly contains the same radial array of outer drive wheels 24 (FIG. 8a). In addition, the intermediate drive assembly contains an intermediate drive wheel 26, an inner drive wheel 28, and the drive shaft 40 as found in the end assembly 20. The intermediate drive support 23 differs from the end support 21 by the absence of the end support lip 22 found on the end support 21.

Figure 9:
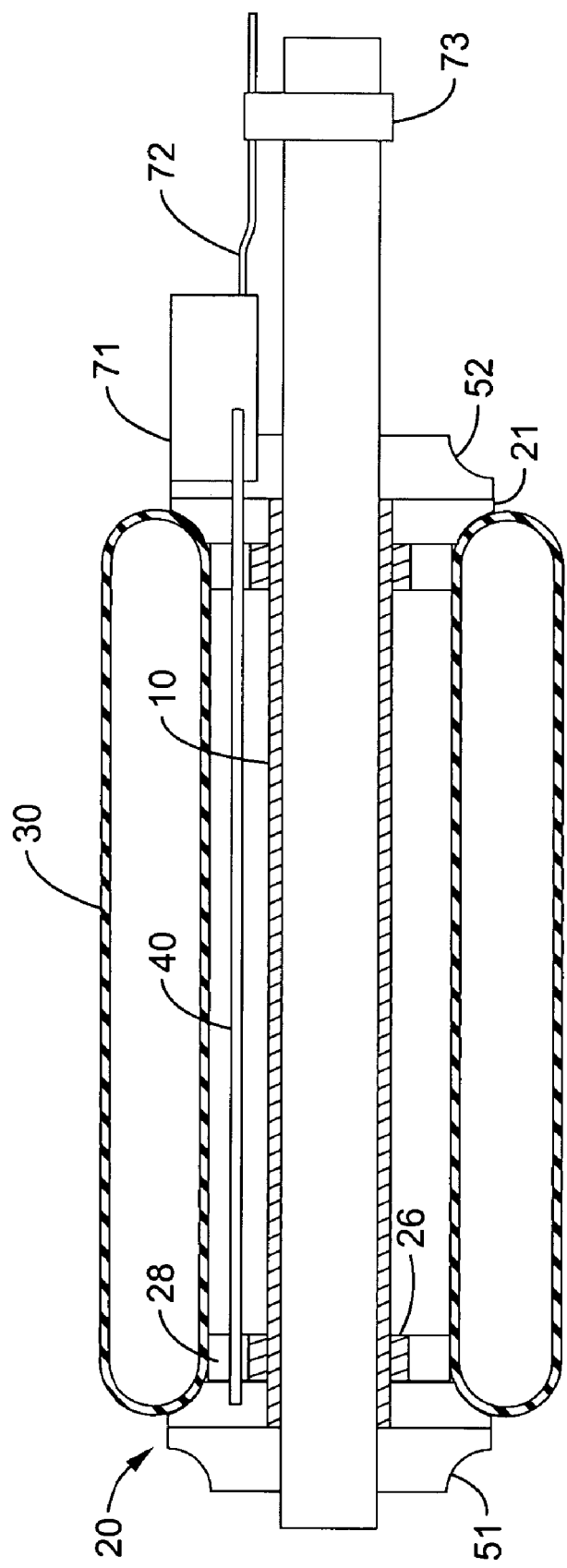
FIG. 9 shows a schematic illustration of certain aspects of another endoscope delivery system of the invention that includes an internal drive motor and an air motor attached to the drive unit.

The additional embodiment is shown in FIG. 9 wherein the external drive unit is replaced by an internal drive unit 70. One such embodiment may include, in a further more detailed illustrative embodiment, the use of an air motor 71 to produce rotational energy as part of the internal drive unit 70 (FIG. 9). In this embodiment, the drive shaft 40 is replaced by an air hose 72 to supply pressure to drive the air motor 71.

It is to be appreciated that the foregoing embodiments herein shown and described by reference to FIGS. 1-9, while highly beneficial, provide illustrative examples of certain specific features and components that are adapted to achieve the various broad aspects, modes, and objects of the invention also herein described. Other approaches than those specified for those particular embodiments are also contemplated. Certain further embodiments are thus provided for further illustration as follows and by reference to FIGS. 10-19.

As explained above for the foregoing embodiments, the following further embodiments of the present invention also provide highly beneficial delivery assemblies that are particularly well suited to propel endoscopes through body lumens in highly beneficial and novel manners. Furthermore, as also elsewhere herein described, such delivery assemblies may be incorporated directly with endoscope assemblies in fixed or secured combination systems. Or, the delivery assemblies may be provided separately in a configuration that is adapted for cooperative engagement and use with endoscopes as separate, though cooperating, devices in an overall system. For the purpose of providing a thorough understanding, the following embodiments are herein shown and described in detail in the context of the latter configuration. In this context, for example, a delivery assembly is thus provided that is adapted for cooperative engagement and use with a separate endoscope 100 as shown schematically with regards to its working distal end portion 102 in FIG. 10.

One particular further beneficial embodiment is shown in various levels of detail in FIGS. 11-17B, which should be read together where appropriate for further understanding of the system and method described.

More specifically, as shown in FIG. 11, the delivery assembly according to the present embodiment of the invention includes a carriage assembly 110 that includes a tubular body 121 that is adapted to be positioned coaxially over distal end portion 102 of endoscope 100. Tubular body 121 includes a proximal end portion 122 and a distal end portion 126, that are each shown to include tapered tips 123,125, respectively in order to provide substantially smooth transition along endoscope 100. An outer circumferential surface 129 extends between proximal and distal end portions 122,126. In addition, proximal and distal stops 120,121, respectively are also provided, and may be either integral with tubular body 121, or assembled thereon.

As shown in FIG. 12, a grooved drive assembly 130 is positioned coaxially around outer surface 129 in a manner allowing substantial rotation of drive assembly 130 while carriage assembly 110 remains substantially fixed along the rotational axis and on endoscope 100. Grooved drive assembly 130 includes a helical groove 132 extending between its ends 133,135 that are positioned to correspond with proximal and distal end portions 122,126, respectively, and in particular between proximal and distal stops 120,121, respectively, of carriage assembly 110. In order to provide such axially contained positioning, at least one of stops 120,121, may be assembled onto tubular member 121 after first positioning grooved drive assembly 130 in the position shown.

A drive gear 136 is shown with a substantially flexible, yet substantially torqueable, drive shaft 137 that extends proximally from a distal coupler 139. Distal coupler 139 is shown to be of a rotational toothed gear type and is adapted to be positioned at least in part within the slotted, toothed rotational gear surface shown at proximal end 133 of drive assembly 130.

As also further shown in the transverse partially cross-sectioned view in FIG. 13, the distal coupler 139 is constructed and geared to drive assembly 130 in a manner such that rotation of drive gear 136 translates into rotation of drive assembly 130 around carriage assembly 110. It is to be appreciated that the interfacing and cooperation between drive gear 136 and drive assembly 130 is provided by means of certain structural supports in a housing assembly, not shown hear in order to provide sufficient view and detail of their functional inter-cooperation. However, such support structures may include, for example, a sheath positioned around drive gear 136 and extending to, and possibly coupled, engaged, or secured with, carriage assembly 110 or other connecting component(s). Or, these various components may be incorporated into the semi-flexible shaft of the related endoscope, such as for example various lumens provided therein, in such an integrated embodiment if so desired.

As further shown in FIG. 14A, a longitudinally slotted cowling 140 is provided co-axially over grooved drive assembly 130. Cowing 140 includes a plurality of longitudinal grooves 146 that extend between a proximal end 142 and a distal end 146 that are positioned to correspond with proximal and distal end portions 122,126 of carriage assembly 110. As further shown in FIG. 14B, four of these grooves 146 are provided in uniformly spaced, 90 degree separated positions around the longitudinal axis L of the assembly. It is to be appreciated that the embodiment herein shown and described in particular detail provides a highly beneficial arrangement, as will be explained in further detail below. However, other numbers, shapes, dimensions, or relative positioning between grooves may be employed to meet a particular need.

Figure 15A:
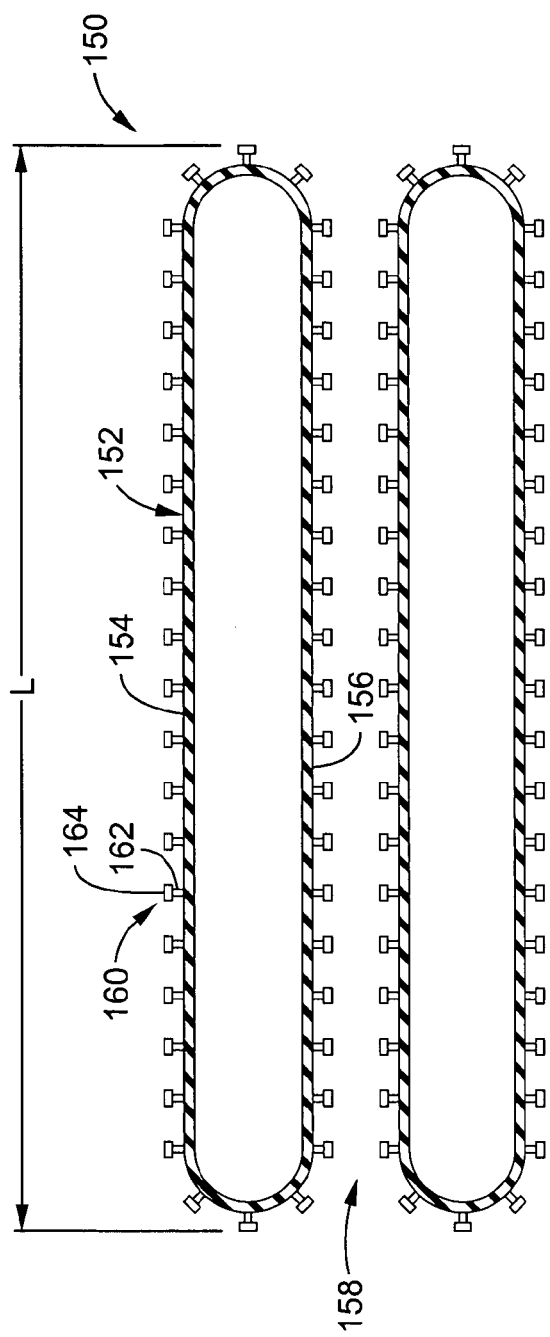
FIG. 15A shows a longitudinally cross-sectioned side view of an annular invaginated balloon as a further component adapted for coordinated use with the variously coupled assemblies and components shown in FIGS. 11-14B.
Figure 15B:
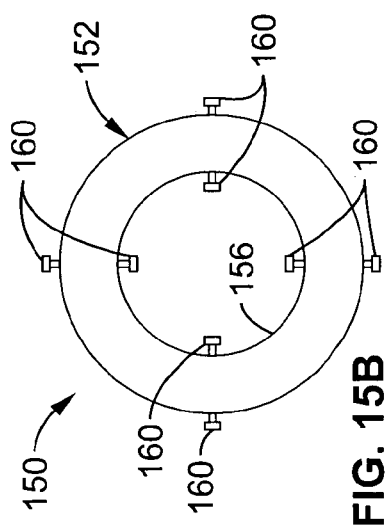
FIG. 15B shows an end view of an annular invaginated balloon similar to that shown in FIG. 15A.

FIG. 15A shows a longitudinally cross-sectioned side view of an annular invaginated balloon 150 as a further component adapted for coordinated use with the variously coupled assemblies and components shown in FIGS. 11-14B. More specifically, balloon 150 includes an outer wall with outer surface 154 surrounding an inner wall with inner surface 156. A plurality of coupling feet 160 are provided in longitudinally patterned groups so as to provide a continuous array around a circumferential pattern extending along outer and inner surfaces 154,156, respectively. The feet 160 include a neck 162 that is relatively more narrow than a head 164. This allows for engaged coupling around neck 162 by a respective drive assembly whereas head 164 prevents mechanical disengagement from such coupling. Feet 160 that are located within lumen 158 surrounded by balloon 150 are coupled in this manner. One particular embodiment includes four such longitudinally and circumferentially spaced arrays of feet that are spaced 90 degrees apart, as shown in FIG. 15B.

Figure 16:
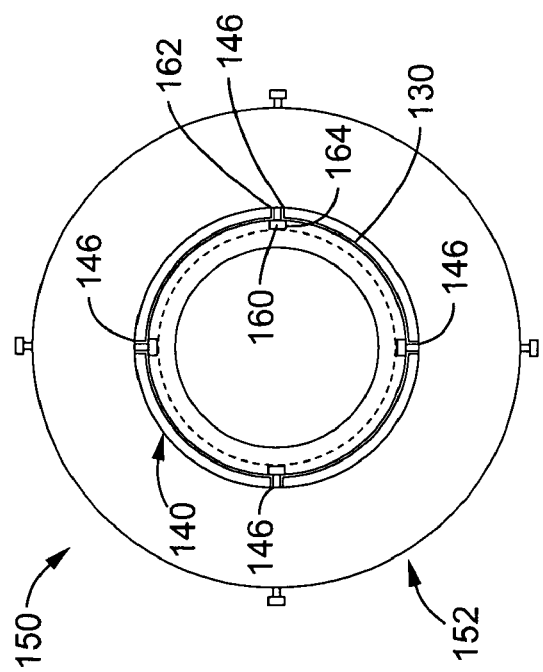
FIG. 16 shows a schematic transversely cross-sectioned view through a coupled assembly that includes the various components shown in FIGS. 11-15B.

As shown in FIG. 16, the spaced arrays of feet 160 of balloon 150 are oriented so as to couple with grooved drive assembly 130 as follows. Each head 164 is positioned within a groove of drive assembly 130 with neck 162 extending through slots 146 of cowling 140. In this manner, rotation of grooved drive assembly 130 translates feet 160 longitudinally along grooves 146, which translates inner wall 156 longitudinally in one direction, and conversely and responsively outer wall 154 translates longitudinally in the opposite direction.

Various methods and materials may be employed to manufacture these various components just described, including in particular balloon 150. However, in order to provide further more detailed illustration for a complete and thorough understanding of the various aspects herein contemplated, one particular more detailed embodiment is provided as follows.

Figure 17A:
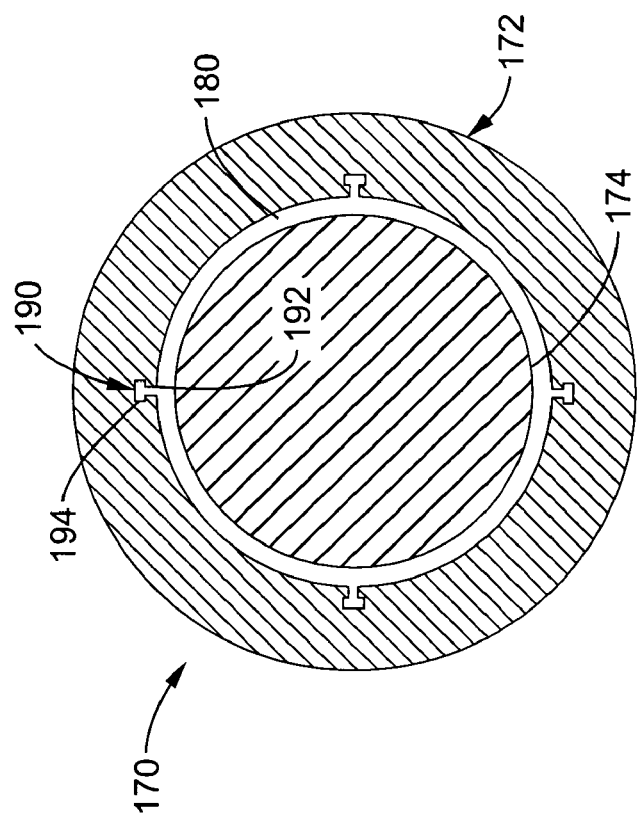
FIGS. 17A and 17B show transversely cross-sectioned and longitudinal side views, respectively, of an assembly adapted for use in manufacturing the annular invaginated balloon shown in FIGS. 15A-16.
Figure 17B:
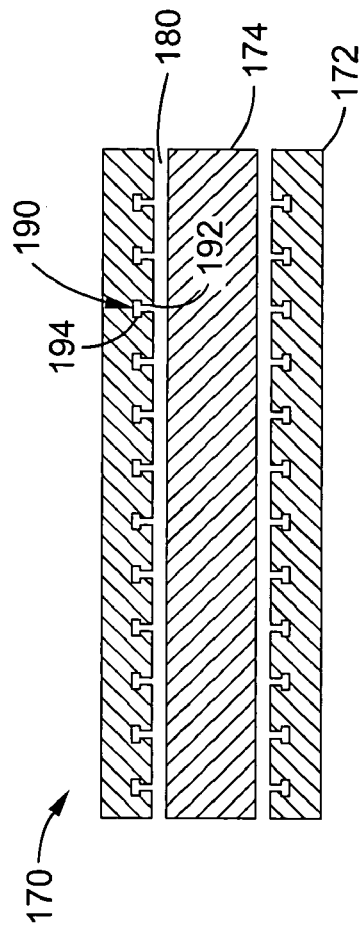

As shown in FIG. 17A and FIG. 17B in various cross-sections, a mold 170 may be used for injection molding a tubular member that includes feet as just described, which tubular member is inverted or everted onto itself such that by securing the opposite ends to each other the annular invaginated balloon such as balloon 150 may result. More specifically, an outer shell mold or die 172 includes an inner annular surface that defines an interior opening or passageway 180. This inner surface includes a plurality of circumferentially and longitudinally spaced cavities 190 that form the negative impression of the intended feet 160, including open neck 192 and head 194 that correspond with neck 162 and head 164 of the intended feet 160. An additional interior mold member or mandrel 174 is positioned within passageway 180 within die 172 in a manner leaving a circumferential and longitudinal annular gap therebetween. The result provides a continuous space as a mold within which a thermoset, thermoplastic, or other polymer or injectable compound may be injected. Upon cooling or otherwise setting in the shape provided by this space, the desired tubing with external feet arrays results and may be inverted or everted to form the balloon as previously described above.

It is to be appreciated, as shown in partial schematic cross-section in FIG. 18, that regardless of the particular drive assembly or coupling mechanism used to translate longitudinal motion of the annular tracking balloon, such balloon beneficially includes an inflation assembly. This is shown schematically in FIG. 18, including an inflation assembly 200 with an inflation or injection needle 210 engaged within a self-sealing valve 230 of balloon 250 via a coupler 220. To deflate the balloon 250, the self sealing valve 230 may be again registered with the coupler 220, or balloon 250 may simply be "popped" by puncturing its wall with needle 210 or by other means for balloon rupture or deflation, as would be apparent to one of ordinary skill.

It is to be appreciated that other drive mechanisms and relative coupling between components may be used to accomplish various objectives herein described.

Figure 19:
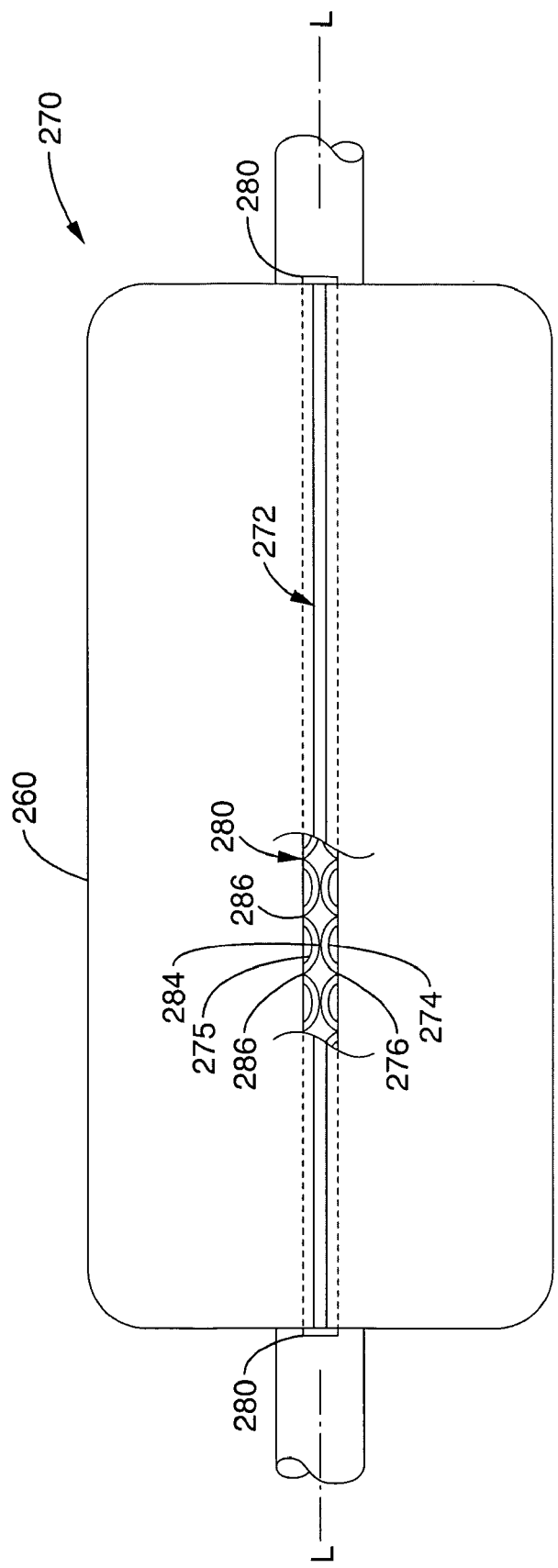
FIG. 19 shows a partially cross-sectioned side view of the embodiment shown in FIG. 18 in order to illustrate other functional details of the assembly.

In one particular further embodiment shown in FIG. 19, an endoscopic propulsion assembly 260 includes an annular invaginated balloon 270 that includes one or more circumferential grooves 272 extending along the longitudinal axis L of balloon 270. Grooves 272 include an interior wall that is shaped with a series of paired, opposite inward protrusions 274,275 spaced at generally regular intervals to thus provide alternating gaps 276 between such paired protrusions. A belt assembly 280 is engaged within groove 272 and includes an array of longitudinally spaced enlargements 286 separated by relatively more narrow waist regions 284. This shape for belt 280 is adapted to correspond with the shaped interior space of groove 272 as shown in FIG. 19. Accordingly, by coupling belt assembly 280 to a drive assembly interiorly of the annular invaginated balloon, such as a grooved drive chassis as previously described above, belt 280 may be rotated longitudinally to thereby drive and translate balloon 270 into longitudinal rotational motion.

The annular invaginated balloon embodiments herein shown and described are hereby further defined as providing a "toroidal" shape in the sense that the balloon appears as a toroid in end-view, although including an extended length along the longitudinal axis encircled by that toroid. Moreover, the rotation imparted to such shape according to the various embodiments is defined as a "toroidal rotation", which is intended to mean the interior surface of the toroidal balloon translates in one longitudinal direction with the exterior surface translating in a second opposite longitudinal direction, thus the toroidal balloon rotates longitudinally around itself. Furthermore, a "side" or "lobe" of the toroidal balloon is intended to mean one circumferential location around the toroid when taken by reference to a transverse cross-section, whereas two opposite sides or lobes constitute two opposite circumferential locations relative to the cross-sectional reference plane transverse to the longitudinal axis encircled by the elongated toroid.

Additional modifications or improvements may be made by the embodiments shown and described herein without departing from the intended scope of the invention which is considered to be broadly beneficial according to various independent aspects described. For example, various modifications to or combinations with the present embodiments may be made in view of other available information to one of ordinary skill in the art upon review of this disclosure and remain within the intended scope of the invention.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. An endoscope propulsion device assembly, comprising:
a toroidal wall having an exterior surface and an interior surface that circumscribes an interior passageway extending along a longitudinal axis, and with a length between a proximal end and a distal end relative to the longitudinal axis;
a drive assembly comprising an end support on each of its proximal and distal ends, wherein the end supports maintain the toroidal wall at a single position along an endoscope during movement of the propulsion device assembly through a body lumen by way of movement of the toroidal wall; and
an endoscope coupler assembly;
wherein the toroidal wall is adjustable from a radially collapsed condition to a radially extended condition, respectively, transverse to the longitudinal axis, wherein the toroidal wall and drive assembly remain coupled in both the radially collapsed condition and the radially extended condition;
wherein the toroidal wall defines an inner volume for adjusting from a radially collapsed condition to a radially extended condition, and wherein the inner volume does not comprise any mechanical elements for propulsion of the device;
wherein the drive assembly is adapted to couple to the toroidal wall and to impart toroidal rotation onto the toroidal wall in the radially extended condition such that the interior surface translates in a first longitudinal direction and the exterior surface translates in a second opposite longitudinal direction along the longitudinal axis; and
wherein the endoscope coupler assembly is adapted to couple the toroidal wall to an endoscope extending along the interior passageway such that the toroidal wall and endoscope are adapted to be propelled together in the first direction along a body lumen during toroidal rotation of the toroidal wall when the exterior surface is engaged to a wall of the body lumen with translating force against the wall.

2. The assembly of claim 1, wherein the toroidal wall comprises:
a toroidal balloon having an annular invaginated balloon wall and that is inflatable from the radially collapsed condition to the radially extended condition with a pressurized fluid.

3. The assembly of claim 2, wherein:
the toroidal balloon comprises a protrusion extending from the balloon wall along the interior surface and into the interior passageway;
the drive assembly comprises an elongate screw extending along the longitudinal axis within the interior passageway and with a helical groove extending helically around the longitudinal axis; and the helical groove is adapted to receive the protrusion within the interior passageway such that rotation of the elongate screw advances the protrusion longitudinally in the first direction along the longitudinal axis, and thereby is adapted to move the Interior surface in the first direction along the longitudinal axis to impart toroidal rotation to the toroidal balloon along the longitudinal axis.

4. The assembly of claim 3, wherein the protrusion extends from the interior surface with a relatively narrow neck and terminates interiorly within the interior passageway with an enlarged head relative to the neck.

5. The assembly of claim 3, further comprising:

a plurality of said protrusions in a patterned group that are each spaced along a longitudinal pattern that circumscribes one lobe of the toroidal balloon along the longitudinal axis;

wherein the toroidal balloon comprises at least one lobe;

wherein each protrusion of the group along the interior surface is engaged to a respective turn of the helical groove and translates longitudinally in the first direction along the rotating screw;

wherein each said protrusion of the group along the inner surface is released therefrom the helical groove when it is translated in the first direction to a first end of the screw;

wherein each said protrusion of the group along the exterior surface translates in the second opposite direction and is adapted to rotate inwardly to the inner surface and to be engaged within the helical groove of the screw at a second end thereof; and wherein continuous rotation of the screw continuously releases and engages respective protrusions of the patterned group at the first and second ends of the screw, respectively, to thereby continuously drive toroidal rotation of the toroidal balloon.

6. The assembly of claim 5, comprising:

a plurality of said groups of protrusions in patterned arrays; and wherein each of the groups of protrusions is located at a unique respective position around a circumference of the toroidal balloon transverse to the longitudinal axis.

7. The assembly of claim 5, comprising:

four of said groups; and wherein the four groups are spaced at 90 degree intervals around the circumference transverse to the longitudinal axis.

8. The assembly of claim 5, further comprising:

a cowling with a substantially tubular body located between the screw and the interior surface of the toroidal balloon and with a longitudinal groove extending along the longitudinal axis between first and second ends of the screw; and wherein the protrusions are adapted to engage the helical groove of the screw through the longitudinal groove of the cowling.

9. The assembly of claim 6, further comprising:

a cowling with a substantially tubular body located between the screw and the interior surface of the toroidal balloon and with a plurality of longitudinal grooves extending along the longitudinal axis between first and second ends of the screw; and wherein the protrusions of each group are adapted to engage the helical groove of the screw through a respective one of the plurality of longitudinal grooves of the cowling.

10. The assembly of claim 2, further comprising:

an expansion actuator that is adapted to couple to the toroidal wall and expand the toroidal wall from the radially collapsed condition to the radially extended condition.

11. The assembly of claim 1, further comprising:

a motor that is adapted to couple to the drive assembly and to actuate the drive assembly coupled to the toroidal wall to impart toroidal rotation to the toroidal wall.

12. The assembly of claim 1, further comprising an endoscope.

13. The assembly of claim 12, wherein said endoscope and the toroidal wall are permanently secured in a fixed position relative to each other via the endoscope coupler assembly.

14. The assembly of claim 12, wherein said endoscope and toroidal wall are adapted to be releasably coupled to each other via the endoscope coupler assembly.

15. The assembly of claim 1, wherein:

the endoscope coupler assembly comprises a base with a tubular member with an inner lumen extending along a length between first and second ends, and further comprises first and second radial protrusion stops extending radially outwardly from the tubular member transverse to the longitudinal axis at each of the first and second ends, respectively;

the base is adapted to be coupled to an endoscope extending along the inner lumen;

the toroidal wall is adapted to be positioned at a location along the base with the tubular member located within the interior passageway and such that in the radially extended condition the toroidal wall has an inner diameter at the interior surface that is less than an outer diameter of the base at the first and second radial protrusion stops; and the toroidal wall is adapted to undergo toroidal rotation at the position without substantially moving longitudinally along the base due to mechanical interference between the toroidal wall and the first and second radial protrusion stops.

16. The assembly of claim 2, wherein:

the toroidal balloon comprises at least one lobe;

the drive assembly comprises a belt that circumscribes one lobe of the toroidal balloon wall along the longitudinal axis and at a position around the circumference transverse to the longitudinal axis;

the toroidal balloon wall comprises a circumferential groove along the longitudinal axis and corresponding with the position;

the belt is adapted to engage the circumferential groove along the exterior surface of the toroidal balloon wall at the position;

the belt is also adapted to engage the drive assembly located within the interior passageway; and the drive assembly is adapted to rotate the belt around the toroidal balloon and so as to impart translational motion to the exterior surface in the second direction to thereby provide toroidal rotation of the balloon.

17. The assembly of claim 16, wherein:

the groove comprises a shaped interior surface with a plurality of spaced pairs of opposite protrusions into the groove to provide an alternating pattern of expanded and narrowed waste regions along the groove;

the belt comprises a shaped outer surface with a plurality of enlargements separated by relatively narrowed waste regions;

the belt and groove are adapted to couple along the exterior surface with the narrowed waste regions of the belt fitting into the narrowed waste regions of the groove; and the belt is adapted to be released from the groove at first and second ends of the exterior surface along the balloon.

18. The assembly of claim 1, wherein the toroidal wall comprises an elongated toroidal wall such that the length is substantially greater than a profile diameter between the interior and exterior surfaces of the toroidal wall in the radially extended condition.

19. A method for propelling an endoscope, comprising:

coupling a toroidal wall to an endoscope at a location along a distal end portion of the endoscope;

coupling a drive assembly to the toroidal wall at the location;

adjusting the toroidal wall from a radially collapsed condition to a radially extended condition, respectively, transverse to the longitudinal axis at the location, wherein the toroidal wall and drive assembly remain coupled in both the radially collapsed condition and the radially extended condition, and wherein the toroidal wall defines an inner volume for adjusting from the radially collapsed condition to the radially extended condition, and wherein the inner volume does not comprise any mechanical elements for propulsion of the endoscope;

actuating the drive assembly to impart toroidal rotation onto the toroidal wall in the radially extended condition at the location such that the interior surface translates in a first longitudinal direction and the exterior surface translates in a second opposite longitudinal direction along the longitudinal axis; and substantially maintaining the toroidal wall at the location along the endoscope while imparting the toroidal rotation to the toroidal wall.

20. The method of claim 19, further comprising:

inserting the endoscope and respectively coupled toroidal wall and drive assembly into a body lumen of a patient;

engaging a lumen wall of the body lumen with the exterior surface of the toroidal wall in the radially extended condition; and propelling the toroidal wall and endoscope together in the first longitudinal direction along the body lumen by imparting the toroidal rotation to the toroidal wall and thereby translating the exterior surface with force in the second opposite direction against the respectively engaged body lumen wall.

21. A method for performing endoscopy within a body lumen in a patient, comprising:

inserting an endoscope assembly within the body lumen;

engaging a substantial circumference of a body lumen wall of the body lumen surrounding the endoscope with a drive assembly coupled to the endoscope, wherein the drive assembly comprises a toroidal balloon that physically links the endoscope to the body lumen, wherein the toroidal balloon defines an inner volume for adjusting from a radially collapsed condition to a radially extended condition, wherein the inner volume does not comprise any mechanical elements for propulsion of the device, and wherein the toroidal balloon is maintained substantially at the same location along the endoscope as it is propelled along the body lumen;

providing an axial force against the body lumen wall and around the substantial circumference with the drive assembly; and propelling the endoscope along the body lumen at least in part using the axial force against the body lumen wall from the drive assembly.

* * * * *